United States Patent
Okada et al.

(10) Patent No.: US 11,786,414 B2
(45) Date of Patent: Oct. 17, 2023

(54) TAPE-TYPE DISPOSABLE DIAPER, AND METHOD FOR MANUFACTURING TAPE-TYPE DISPOSABLE DIAPER

(71) Applicant: Daio Paper Corporation, Ehime (JP)

(72) Inventors: Yuki Okada, Ehime (JP); Masashi Furukawa, Ehime (JP); Yosuke Mori, Ehime (JP)

(73) Assignee: Daio Paper Corporation, Ehime (JP)

( * ) Notice: Subject to any disclaimer, the term of this patent is extended or adjusted under 35 U.S.C. 154(b) by 1052 days.

(21) Appl. No.: 16/491,262

(22) PCT Filed: Mar. 6, 2018

(86) PCT No.: PCT/JP2018/008471
§ 371 (c)(1),
(2) Date: Sep. 5, 2019

(87) PCT Pub. No.: WO2018/180264
PCT Pub. Date: Oct. 4, 2018

(65) Prior Publication Data
US 2020/0038257 A1 Feb. 6, 2020

(30) Foreign Application Priority Data

Mar. 28, 2017 (JP) .................. 2017-063581
Mar. 30, 2017 (JP) .................. 2017-067003

(51) Int. Cl.
| A61F 13/49 | (2006.01) |
| A61F 13/15 | (2006.01) |
| A61F 13/56 | (2006.01) |

(52) U.S. Cl.
CPC .. *A61F 13/49011* (2013.01); *A61F 13/15585* (2013.01); *A61F 13/5622* (2013.01); *A61F 2013/49025* (2013.01)

(58) Field of Classification Search
CPC .. A61F 13/5622; A61F 13/5638; A61F 13/58; A61F 2013/49022;
(Continued)

(56) References Cited

U.S. PATENT DOCUMENTS

| 8,529,536 B2 * | 9/2013 | Tsang ................. B32B 38/00 604/394 |
| 2011/0208149 A1 | 8/2011 | Vastag et al. |
| 2019/0021916 A1 * | 1/2019 | Ishikawa ............ B29C 65/4815 |

FOREIGN PATENT DOCUMENTS

| JP | 2001-095838 | 4/2001 |
| JP | 2001-346827 | 12/2001 |

(Continued)

OTHER PUBLICATIONS

International Search Report for PCT/JP2018/008471, dated Jun. 5, 2018.

*Primary Examiner* — Michele Kidwell
(74) *Attorney, Agent, or Firm* — Andrus Intellectual Property Law, LLP

(57) ABSTRACT

To obtain a wide stretching range in a waist stretching sheet, a tape-type disposable diaper has a main body including a waist stretching sheet and a fastening tape on a dorsal side portion B. The main body has a folded-back portion in which a side including a portion having a non-stretchable region of the waist stretching sheet is folded back to a center side and fixed.

15 Claims, 20 Drawing Sheets

(58) Field of Classification Search
CPC .. A61F 2013/49025; A61F 2013/49055; A61F 2013/49042; A61F 13/49011; A61F 13/49012; A61F 13/49014
See application file for complete search history.

(56) References Cited

FOREIGN PATENT DOCUMENTS

| | | |
|---|---|---|
| JP | 2004-298499 | 10/2004 |
| JP | 2005-152168 | 6/2005 |
| JP | 2008-029749 | 2/2008 |
| JP | 2010-017341 | 1/2010 |
| JP | 2010-022550 | 2/2010 |
| JP | 2011-072736 | 4/2011 |
| JP | 2013-078371 | 5/2013 |
| WO | 2017-006677 | 1/2017 |

\* cited by examiner

FIG.5
(a)
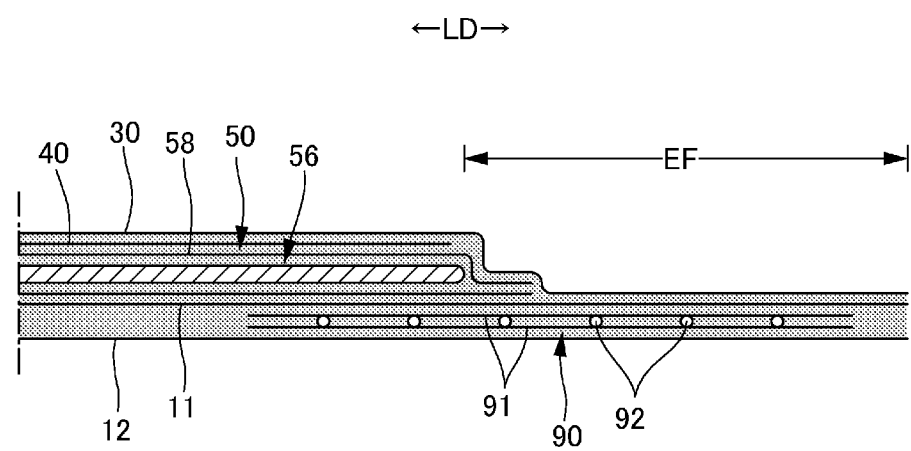
(b)
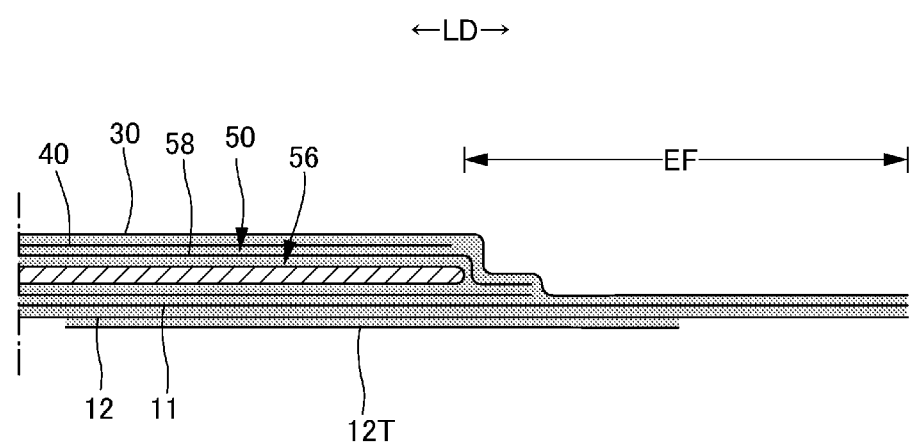

FIG.11
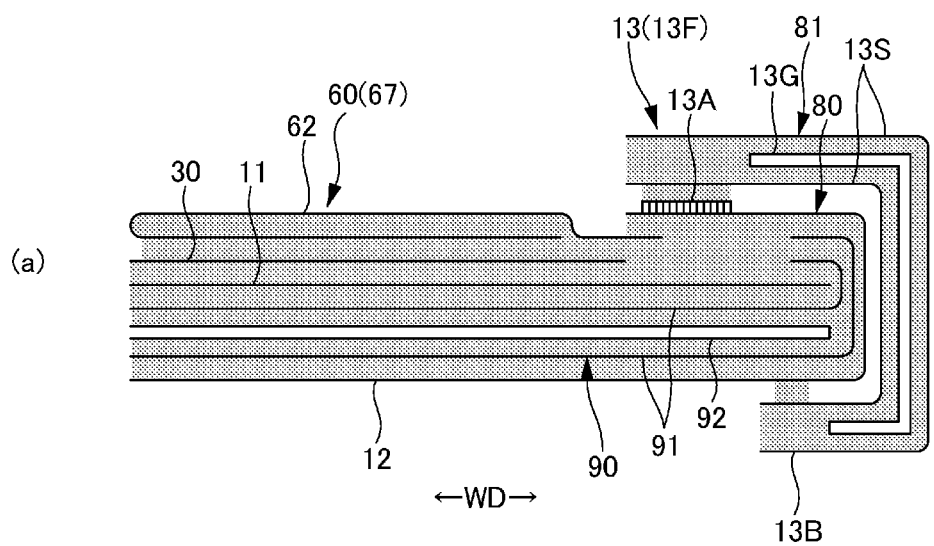
(a)
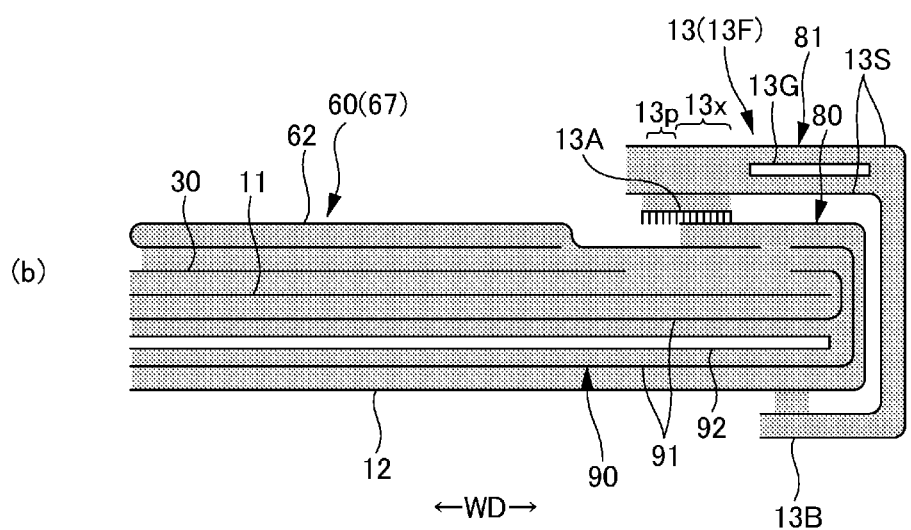
(b)

FIG.12
(a)
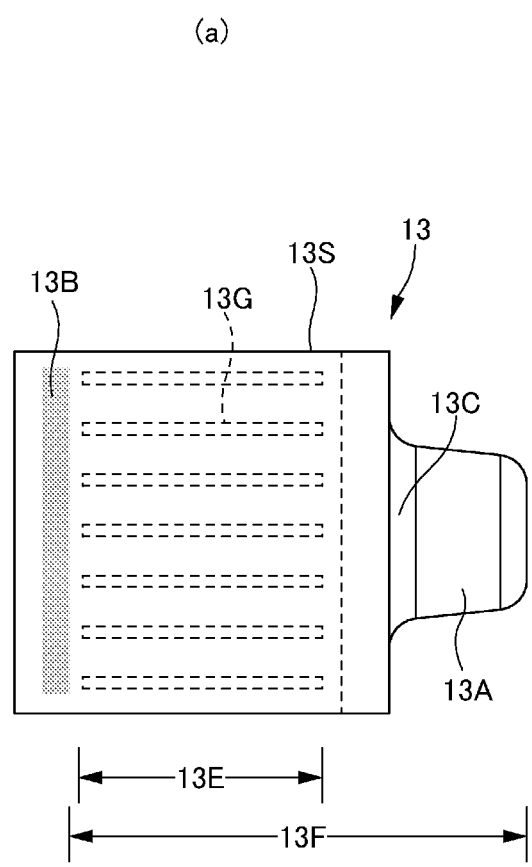
(b)
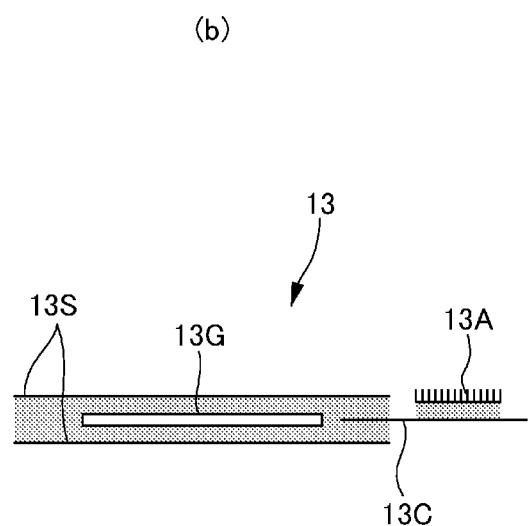

FIG.14
(a)
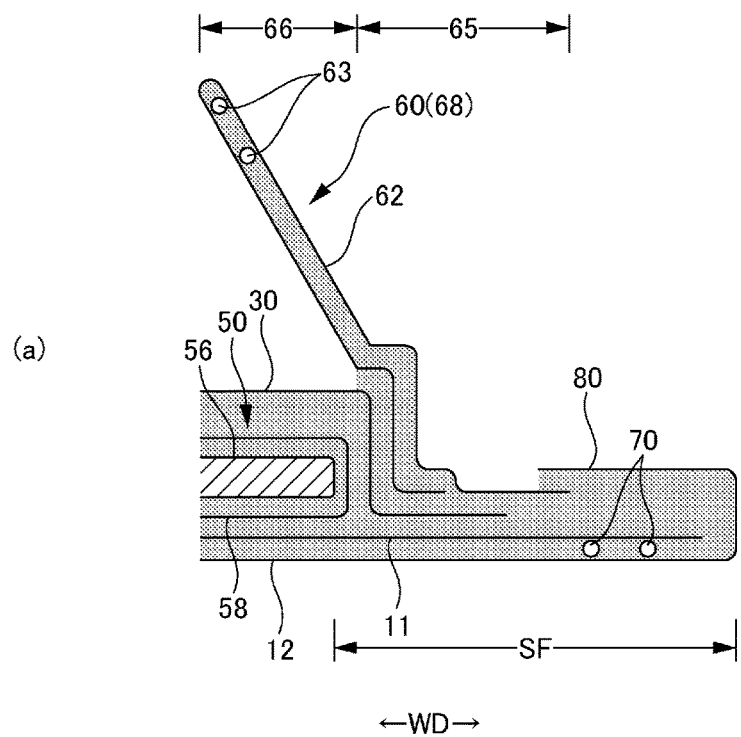
(b)
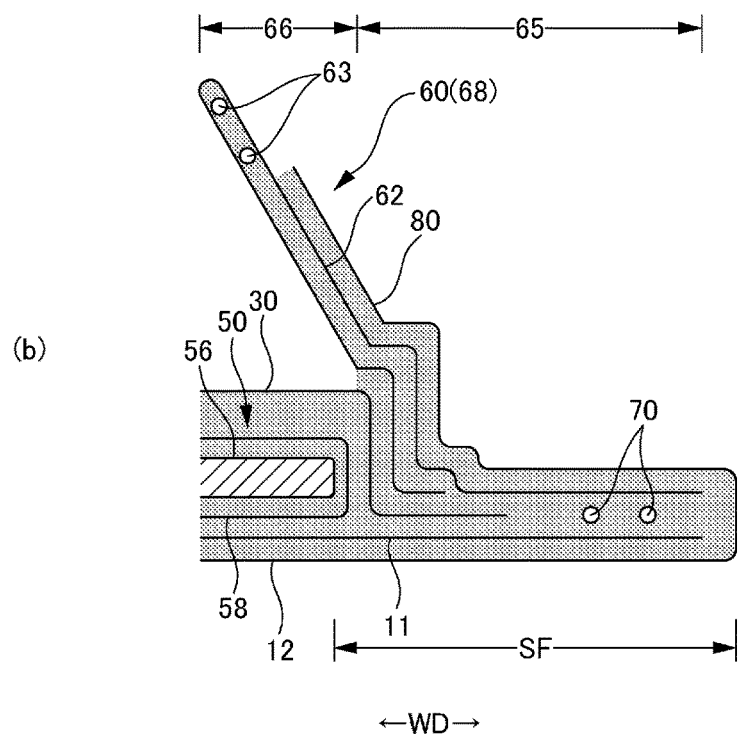

FIG.19
(a)
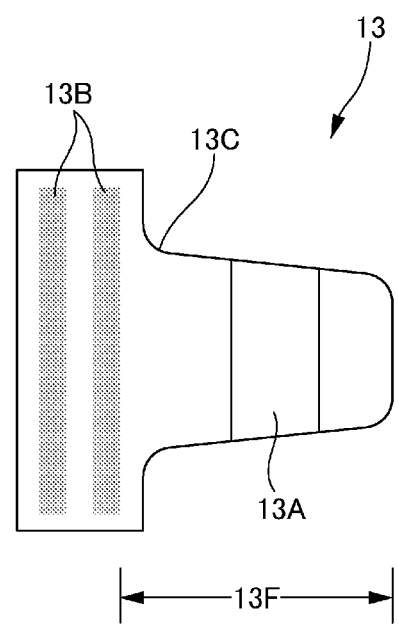
(b)
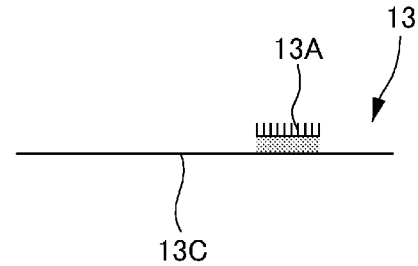

TAPE-TYPE DISPOSABLE DIAPER, AND METHOD FOR MANUFACTURING TAPE-TYPE DISPOSABLE DIAPER

CROSS-REFERENCE TO RELATED APPLICATIONS

This application is the U.S. national stage application of International Application PCT/JP2018/008471, filed Mar. 6, 2018, which international application was published on Oct. 4, 2018, as International Publication WO 2018/180264 in the Japanese language. The International Application claims priority of Japanese Patent Application Nos. 2017-063581, filed Mar. 28, 2017 and 2017-067003, filed Mar. 30, 2017. The international application and Japanese applications are all incorporated herein by reference, in entirety.

TECHNICAL FIELD

The present invention relates to a so-called tape-type disposable diaper and a method of manufacturing the tape-type disposable diaper.

BACKGROUND ART

Mainly, there are three types of disposable diapers of a tape-type, an underpants-type, and a pad-type. Among these diapers, the tape-type disposable diaper is worn by attaching the diaper to a body in an unfolded state and then connecting fastening tapes protruding from both sides of a dorsal side portion to an outer surface of a ventral side portion.

A general tape-type disposable diaper includes: a main body having a ventral side portion extending to a front side of the center in a front-back direction and a dorsal side portion extending to a back side of the center in the front-back direction; and fastening tapes protruding from both side portions of the dorsal side portion, and has a structure in which the fastening tapes are brought to an outer surface of the ventral side portion from both sides of a waist to be connected to an outer surface of the ventral side portion at the time of attaching the diaper to a body. Such a tape-type disposable diaper is used not only for babies but also widely used in nursing applications (adult applications).

The tape-type disposable diaper has poorer fitting in a lower torso direction than an underpants-type disposable diaper. Therefore, it has been proposed to enhance fitting with respect to a lower torso by disposing a stretchable region in a width direction in a lower torso portion of a dorsal side portion or disposing a stretchable region in the width direction in the fastening tape (for example, see Patent Literatures 1 to 3).

In particular, preferably, a stretchable region in the width direction is disposed in a lower torso portion of a dorsal side portion, and a stretchable region in the width direction is disposed in the fastening tape because elasticity can be imparted to a wider range.

However, as described in detail in Patent Literature 3, in a case where a waist stretching sheet having elasticity in a width direction is incorporated in a lower torso portion of a dorsal side portion to form a stretchable region in the width direction, when there is elasticity up to both end portions of the waist stretching sheet in the width direction, wrinkles or curls may be generated in the both end portions of the waist stretching sheet in the width direction at the time of manufacture, and an appearance in a product state may be deteriorated.

Therefore, conventionally, a stretchable region cannot be disposed over the entire waist stretching sheet in the width direction, and sufficient elasticity cannot be imparted to a lower torso only with the waist stretching sheet. In addition, even if stretchable regions are disposed in the fastening tapes, the stretchable regions are separated from each other not a little in the width direction, and it is difficult to form a continuous stretchable region across the left and right fastening tapes.

CITATION LIST

Patent Literature

Patent Literature 1: JP 2010-22550 A
Patent Literature 2: JP 2005-152168 A
Patent Literature 3: JP 2008-29749 A
Patent Literature 4: JP 2011-072736 A

SUMMARY OF INVENTION

Technical Problem

Therefore, a main object of the present invention is to make it possible to widen a stretching range of a waist stretching sheet in order to enhance fitting with respect to a lower torso.

Solution to Problem

Representative aspects of the present invention solving the above problem are as follows.

<First Aspect>

A tape-type disposable diaper including:

a main body having a ventral side portion extending to a front side from a center in a front-back direction and a dorsal side portion extending to a back side from a center in the front-back direction;

fastening tapes protruding from both side portions of a lower torso portion of the dorsal side portion; and a waist stretching sheet disposed in the lower torso portion of the dorsal side portion, each of the fastening tapes having a base portion attached to the lower torso portion of the dorsal side portion and a connecting portion detachably connected to an outer surface of the ventral side portion, the waist stretching sheet serving as a non-stretchable region at both end portions in the width direction and serving as a main body stretchable region that expands and contracts in the width direction at a portion between the non-stretchable regions, in which the main body has a folded-back portion obtained by folding back a side including a portion having the non-stretchable region to a center side and fixing thereto.

(Action and Effect)

In the present aspect, the portion having the non-stretchable region in the main body is folded back to the center side and fixed. Therefore, the (unavoidably formed) width of the non-stretchable region of the waist stretching sheet occupied in the width of the main body can be reduced. As a result, a stretching range of the waist stretching sheet can be wide.

<Second Aspect>

The tape-type disposable diaper according to the first aspect, in which each of the fastening tapes has a tape stretchable region that is disposed in a portion between the base portion and the connecting portion and expands and contracts in the width direction, and the fastening tapes are attached to the main body such that a base edge of the tape stretchable region is located within a range of ±5 mm in the width direction from a side edge of the main body stretchable region.

(Action and Effect)

In the present aspect, the portion having the non-stretchable region in the main body is folded back to the center side and fixed. Therefore, the (unavoidably formed) width of the non-stretchable region of the waist stretching sheet occupied in the width of the main body can be reduced. As a result, continuity of the stretchable region across the left and right fastening tapes can be improved.

<Third Aspect>

The tape-type disposable diaper according to the second aspect, in which the main body includes:

an absorber;

a liquid impervious sheet covering a back surface side of the absorber;

an outer sheet covering a back surface side of the liquid impervious sheet;

side flap portions each located outside a side edge of the absorber; and a rising gather including: a gather sheet forming a root portion fixed to a region including each of the side flap portions, and a protruding portion extending from the root portion; a fallen portion in which both end portions of the protruding portion in a front-back direction are fixed in a fallen state; a non-fixed rising portion located between front and back fallen portions in the protruding portion; and a gather elastic member fixed in a state of being stretched in the front-back direction at least at a tip portion of the rising portion, the main body stretchable region in the waist stretching sheet extends across the left and right side flap portions, each of the side flap portions is a portion in which the gather sheet, the liquid impervious sheet, the waist stretching sheet, and the outer sheet are stacked, the folded-back portion is formed in each of the side flap portions and is a portion in which the gather sheet, at least a part of the non-stretchable region of the waist stretching sheet, and the outer sheet are folded back to a front surface side, and a base portion of each of the fastening tapes is attached to a back surface of a portion having the folded-back portion in each of the side flap portions.

(Action and Effect)

In a case where such a portion having the waist stretching sheet and the fastening tape as in the present aspect is included, the folded-back portion can have such a structure as in the present aspect. In this case, by attaching the base portion of the fastening tape to a back surface of a portion having the folded-back portion in the side flap portion, not only the strength of a portion where a force is concentrated during use (a portion where the fastening tape is attached) is high, but also no force to peel off the folded-back portion is applied advantageously. Alternatively, by attaching no base portion of the fastening tape to a skin side, a texture of a surface on the skin side is not impaired.

<Fourth Aspect>

The tape-type disposable diaper according to the second aspect, in which the main body includes:

an absorber;

a liquid impervious sheet covering a back surface side of the absorber;

an outer sheet covering a back surface side of the liquid impervious sheet;

side flap portions each located outside a side edge of the absorber; and a rising gather including: a gather sheet forming a root portion fixed to a region including each of the side flap portions, and a protruding portion extending from the root portion; a fallen portion in which both end portions of the protruding portion in a front-back direction are fixed in a fallen state; a non-fixed rising portion located between front and back fallen portions in the protruding portion; and a gather elastic member fixed in a state of being stretched in the front-back direction at least at a tip portion of the rising portion, the main body stretchable region in the waist stretching sheet extends across the left and right side flap portions, each of the side flap portions is a portion in which the gather sheet, the liquid impervious sheet, the waist stretching sheet, and the outer sheet are stacked, the folded-back portion is formed in each of the side flap portions and is a portion in which at least a part of the non-stretchable region of the waist stretching sheet and the outer sheet are folded back to a front surface side, a front surface side of the folded-back portion is covered with a side of the gather sheet, and a base portion of each of the fastening tapes is attached between the folded-back portion and a side of the gather sheet in each of the side flap portions.

(Action and Effect)

In a case where such a portion having the waist stretching sheet and the fastening tape as in the present aspect is included, the folded-back portion can have such a structure as in the present aspect. In this case, by attaching the base portion of the fastening tape to a folded-back portion of the side flap portion, the strength of a portion where a force is concentrated during use (a portion where the fastening tape is attached) is high. Alternatively, the base portion of the fastening tape is not exposed, and a hard material such as the outer sheet is not exposed due to covering of the front surface side of the folded-back portion with the side of the gather sheet. Therefore, a texture is not impaired.

<Fifth Aspect>

The tape-type disposable diaper according to the second aspect, in which the main body includes:

an absorber;

a liquid impervious sheet covering a back surface side of the absorber;

an outer sheet covering a back surface side of the liquid impervious sheet;

side flap portions each located outside a side edge of the absorber; and a rising gather including: a gather sheet forming a root portion fixed to a region including each of the side flap portions, and a protruding portion extending from the root portion; a fallen portion in which both end portions of the protruding portion in a front-back direction are fixed in a fallen state; a non-fixed rising portion located between front and back fallen portions in the protruding portion; and a gather elastic member fixed in a state of being stretched in the front-back direction at least at a tip portion of the rising portion, the main body stretchable region in the waist stretching sheet extends across the left and right side flap portions, each of the side flap portions is a portion in which the gather sheet, the liquid impervious sheet, the waist stretching sheet, and the outer sheet are stacked, the folded-back portion is formed in each of the side flap portions and is a portion in which the gather sheet, at least a part of the non-stretchable region of the waist stretching sheet, and the outer sheet are folded back to a front surface side, and a base portion of each of the fastening tapes is attached to a back surface of a portion having the folded-back portion in each of the side flap portions.

(Action and Effect)

In a case where such a portion having the waist stretching sheet and the fastening tape as in the present aspect is included, the folded-back portion can have such a structure as in the present aspect. In this case, by attaching the base portion of the fastening tape to a folded-back portion of the side flap portion, the strength of a portion where a force is concentrated during use (a portion where the fastening tape is attached) is high. In addition, by forming the front surface side of the folded-back portion with a gather sheet and attaching no base portion of the fastening tape to a skin side, a texture of a surface on the skin side is not impaired.

<Sixth Aspect>

The tape-type disposable diaper according to any one of the third to fifth aspects, in which the folded-back portion does not include the liquid impervious sheet.

(Action and Effect)

The folded-back portion increases a thickness thereof and tends to be hard, and therefore preferably has a structure not including a liquid impervious sheet that particularly tends to be hard.

<Seventh Aspect>

The tape-type disposable diaper according to any one of the first to sixth aspects, in which each of the fastening tapes has the base portion fixed to a back surface of the main body and a fastener free portion extending in a lateral side from the base portion, the fastener free portion has a fastener folded-back portion folded back to an upper side of the folded-back portion at a side edge of the main body, and the fastener folded-back portion is releasably and temporarily fixed to the folded-back portion of the main body at a portion overlapping with the folded-back portion of the main body.

(Action and Effect)

In the present aspect, the fastening tape is disposed outside the main body, and the base portion of the fastening tape is fixed to the back surface side of the main body. In addition, the main body has the folded-back portion and has the fastener folded-back portion outside the folded-back portion. The fastener folded-back portion is releasably and temporarily fixed to the folded-back portion of the main body. Such a structure can be manufactured, at the time of manufacture, by disposing the fastening tape such that a site serving as a base portion of the fastening tape is located at a site serving as a back surface side of the main body and extends to a site serving as the folded-back portion of the main body in an unfolded state before the folded-back portion of the main body is formed, fixing the site serving as the base portion of the fastening tape to the main body, releasably and temporarily fixing the fastening tape to the site serving as the folded-back portion of the main body, and then folding back both side portions of the main body and the fastening tape integrally to form the folded-back portion of the main body and the fastener folded-back portion. That is, at the time of folding-back, the fastening tape is integrated with the main body at two places of the base portion and the temporarily fixed portion. Therefore, folding back of the fastening tape is unlikely to be unsuitable. As a result, according to the present aspect, it is possible to effectively prevent positional deviation of the folded-back portion of the fastening tape.

Incidentally, the fastener folded-back portion in the fastening tape is only temporarily fixed to the folded-back portion of the main body. Therefore, at the time of use, by releasing the temporary fixing by unfolding the fastener folded-back portion to a lateral side, a portion having the connecting portion in the fastening tape protrudes from a side edge of the folded-back portion of the main body. The diaper according to the present aspect can be used similarly to a conventional one except for inclusion of the folded-back portion in the main body.

<Eighth Aspect>

The tape-type disposable diaper according to the seventh aspect, in which the fastener folded-back portion has the connecting portion at a portion overlapping with the folded-back portion of the main body, the fastener folded-back portion is temporarily fixed to the folded-back portion of the main body by the connecting portion, and the connecting portion has a temporarily fixed portion temporarily fixed to the folded-back portion of the main body and a projecting portion located on a width direction center side of a width direction center side edge of the folded-back portion of the main body and not temporarily fixed to the folded-back portion of the main body.

(Action and Effect)

The entire connecting portion of the fastener folded-back portion may be temporarily fixed to the folded-back portion of the main body. However, as in the present aspect, a part of the connecting portion is preferably located on the width direction center side of the folded-back portion of the main body to form the projecting portion because the connecting portion is easily peeled off when the fastener folded-back portion is unfolded.

<Ninth Aspect>

The tape-type disposable diaper according to the seventh or eighth aspect, in which the main body includes:

an absorber;

a liquid impervious sheet covering a back surface side of the absorber;

an outer sheet covering a back surface side of the liquid impervious sheet;

side flap portions each located outside a side edge of the absorber; and a rising gather including: a gather sheet forming a root portion fixed to a region including each of the side flap portions, and a protruding portion extending from the root portion; a fallen portion in which both end portions of the protruding portion in a front-back direction are fixed in a fallen state; a non-fixed rising portion located between front and back fallen portions in the protruding portion; and a gather elastic member fixed in a state of being stretched in the front-back direction at least at a tip portion of the rising portion, and the gather sheet extends only to an end portion on a width direction center side of the folded-back portion of the main body.

(Action and Effect)

The portion having the folded-back portion in the main body increases a thickness thereof by folding-back and easily impairs air permeability and flexibility. Therefore, the width of the gather sheet is preferably narrowed as in the present aspect because it is possible to reduce a region where the folded-back portion of the main body of the outer sheet overlaps with the gather sheet to increase the thickness and to suppress a decrease in air permeability and flexibility.

<Tenth Aspect>

The tape-type disposable diaper according to the seventh or eighth aspect, in which
the main body includes:
an absorber;
a liquid impervious sheet covering a back surface side of the absorber;
an outer sheet covering a back surface side of the liquid impervious sheet;
side flap portions each located outside a side edge of the absorber; and
a rising gather including: a gather sheet forming a root portion fixed to a region including each of the side flap portions, and a protruding portion extending from the root portion; a fallen portion in which both end portions of the protruding portion in a front-back direction are fixed in a fallen state; a non-fixed rising portion located between front and back fallen portions in the protruding portion; and a gather elastic member fixed in a state of being stretched in the front-back direction at least at a tip portion of the rising portion, and
the folded-back portion of the main body extends to the rising portion of the rising gather and is bonded to the rising gather.

(Action and Effect)

As in the present aspect, when the outer side of the rising portion of the rising gather is covered with the folded-back portion of the main body, the number of stacked layers of a material of the rising gather is increased, and a liquid impervious property can be improved. In particular, the present aspect is suitable in a case where a water shielding film is not incorporated in the rising gather.

<Eleventh Aspect>

The tape-type disposable diaper according to any one of the seventh to tenth aspects, in which
a sheet on a backmost side of the main body is formed of a perforated nonwoven fabric having many holes passing through the sheet from the front to the back at intervals, and at least the folded-back portion of the main body has the many holes.

(Action and Effect)

The portion having the folded-back portion in the main body increases a thickness thereof by folding-back and easily impairs air permeability and flexibility. Therefore, as in the present aspect, the folded-back portion of the main body is preferably formed of the perforated nonwoven fabric having excellent flexibility and air permeability.

<Twelfth Aspect>

The tape-type disposable diaper according to any one of the seventh to tenth aspects, in which
the folded-back portion of the main body is bonded to a sheet adjacent to a back surface side of the folded-back portion of the main body via a hot melt adhesive disposed in an intermittent pattern.

(Action and Effect)

The portion having the folded-back portion in the main body increases a thickness thereof by folding-back and easily impairs air permeability and flexibility. Therefore, as in the present aspect, the folded-back portion of the main body is preferably fixed by intermittent adhesion to suppress a decrease in air permeability and flexibility in a region having the folded-back portion of the main body.

<Thirteenth Aspect>

A method for manufacturing the tape-type disposable diaper according to the seventh aspect, the method including:
disposing the fastening tapes on the main body such that a site serving as a base portion of each of the fastening tapes is located at a site serving as a back surface side of the main body and extends to a site serving as the folded-back portion of the main body in an unfolded state before the folded-back portion of the main body is formed, fixing the site serving as the base portion of each of the fastening tapes to the main body, and releasably and temporarily fixing the fastening tape to the site serving as the folded-back portion of the main body; and
folding back both side portions of the main body and the fastening tapes integrally to form the folded-back portion of the main body and the fastener folded-back portion.

(Action and Effect)

According to the present aspect, it is possible to achieve similar actions and effects to those in the seventh aspect. That is, at the time of folding-back, the fastening tape is integrated with the main body at two places of the base portion and the temporarily fixed portion. Therefore, folding back of the fastening tape is unlikely to be unsuitable. As a result, according to the present aspect, it is possible to effectively prevent positional deviation of the folded-back portion of the fastening tape.

Advantageous Effects of Invention

As described above, according to the present invention, for example, the stretching range of the waist stretching sheet can be wide, and fitting to a lower torso can be enhanced advantageously.

BRIEF DESCRIPTION OF DRAWINGS

FIG. 5(a) is a 7-7 cross-sectional view of FIG. 1, and FIG. 5(b) is an 8-8 cross-sectional view of FIG. 1.

FIG. 11 is an enlarged cross-sectional view illustrating a portion having a waist stretching sheet and a fastening tape in another embodiment.

FIG. 12(a) is a plan view of a fastening tape, and FIG. 12(b) is a cross-sectional view of the fastening tape.

FIG. 14 is an enlarged cross-sectional view of a main part of a side gather portion.

FIG. 19(a) is a plan view of a fastening tape, and FIG. 19(b) is a cross-sectional view of the fastening tape.

DESCRIPTION OF EMBODIMENTS

Figure 1:
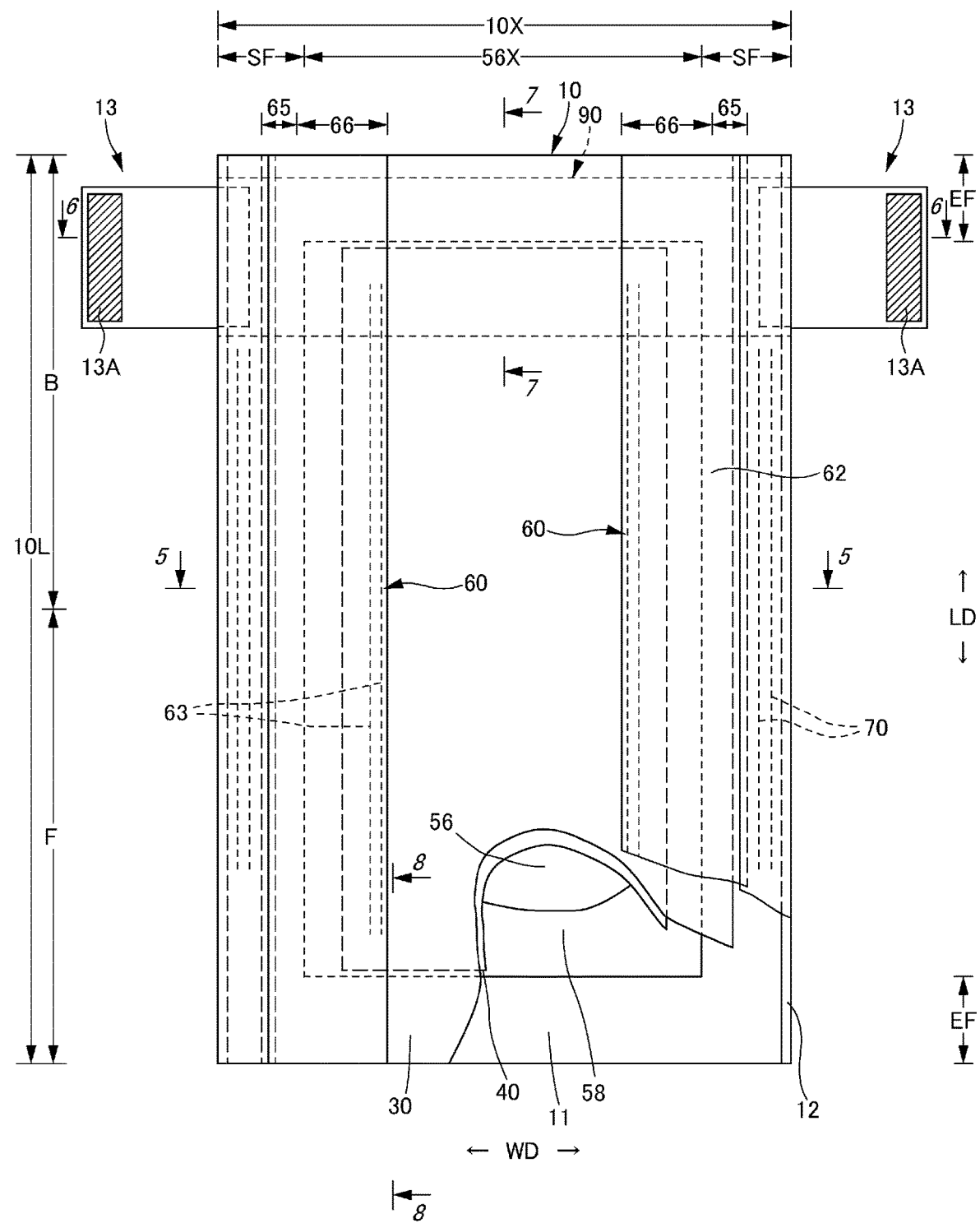
FIG. 1 is a plan view illustrating an inner surface of a tape-type disposable diaper in a state where the diaper is unfolded.

Hereinafter, an embodiment of the present invention will be described with reference to the attached drawings. A dotted pattern portion in the cross-sectional views illustrates a hot melt adhesive for bonding constituent members. However, of course, bonding may be performed using another adhesive or welding such as heat sealing or ultrasonic sealing in place of the hot melt adhesive. In the following description, "front-back direction LD (longitudinal direction)" means a direction connecting a ventral side (front side) and a dorsal side (back side), and "width direction WD" means a direction (horizontal direction) orthogonal to the front-back direction.

FIGS. 1 to 7 illustrate an example of a tape-type disposable diaper. This tape-type disposable diaper includes: a main body 10 having a ventral side portion F extending to a front side of a center C in a front-back direction and a dorsal side portion B extending to a back side of the center C in the front-back direction, and including an absorber 56 disposed in an intermediate portion in the width direction WD from the ventral side portion F to the dorsal side portion B, a liquid pervious top sheet 30 covering a front surface side of the absorber 56, and a liquid impervious sheet 11 covering a back surface side of the absorber 56; and fastening tapes 13 protruding from both side portions of a lower torso portion in the dorsal side portion B in the main body 10 for connecting the ventral side portion F to the dorsal side portion B. The main body 10 has an end flap portion EF extending to front and back sides of the absorber 56 and including no absorber 56, and a side flap portion SF extending to a lateral side of the absorber 56 and including no absorber 56.

(Main Body)

In the main body 10, as in a general tape-type disposable diaper, the width of a lower torso portion of each of the ventral side portion F and the dorsal side portion B may be wider than the width of a crotch portion (in other words, a narrow portion around a leg may be located in an intermediate portion in the front-back direction LD). However, in order to make cutting unnecessary, an embodiment is also preferable in which the width of the diaper is the same as the width of the crotch portion over the maximum length as in the illustrated example (in other words, a rectangular shape having no narrower portion).

More specifically, in the illustrated example, the entire outer surface of the main body 10 is formed of an outer sheet 12, and the liquid impervious sheet 11 is fixed to an internal surface side thereof with an adhesive such as a hot melt adhesive. Furthermore, on an inner surface side of the liquid impervious sheet 11, an absorbent element 50 including the absorber 56, an intermediate sheet 40, and the top sheet 30 are stacked in this order. The top sheet 30 and the liquid impervious sheet 11 are rectangular in the illustrated example, and each have a size slightly larger than the absorbent element 50 in the front-back direction LD and the width direction WD. A peripheral edge portion projecting from a side edge of the absorbent element 50 in the top sheet 30 is fixed to a peripheral edge portion projecting from a side edge of the absorbent element 50 in the liquid impervious sheet 11 with a hot melt adhesive or the like. This portion serves as a part of the end flap portion EF and the side flap portion SF.

Furthermore, on both sides on a surface of the main body 10 in the width direction WD, rising gathers 60 and 60 rising to a skin side of a wearer are disposed. Gather sheets 62 and 62 forming the rising gathers 60 and 60 extend from both sides of the top sheet 30 to the side flap portions SF.

Hereinafter, a material of each portion and a characteristic part thereof will be described sequentially.

(Outer Sheet)

The outer sheet 12 is disposed such that a back surface of the disposable diaper has a texture and an appearance like cloth. A nonwoven fabric is suitable as the outer sheet 12, but the outer sheet 12 is not limited thereto. The type of the nonwoven fabric is not particularly limited. Examples thereof as a material fiber include a synthetic fiber such as a polyolefin-based fiber including polyethylene and polypropylene, a polyester-based fiber, or a polyamide-based fiber, a regenerated fiber such as rayon or cupra, and a natural fiber such as cotton. Examples of a processing method include a spunlacing method, a spunbonding method, a thermal bond method, an air through method, and a needle punching method. However, a long-fiber nonwoven fabric such as a spunbonded nonwoven fabric, an SMS nonwoven fabric, or an SMMS nonwoven fabric is suitable from a viewpoint of achieving both texture and strength. A nonwoven fabric can be used in a single sheet or in a plurality of stacked sheets. In the latter case, the nonwoven fabrics 12 are preferably bonded to each other with a hot melt adhesive or the like. In a case where a nonwoven fabric is used, it is desirable that the nonwoven fabric has a fiber basis weight of 10 to 50 g/m$^2$, particularly 15 to 30 g/m$^2$. The outer sheet 12 can be omitted. In this case, the liquid impervious sheet 11 can be exposed to a back surface of the disposable diaper.

(Liquid Impervious Sheet)

A material of the liquid impervious sheet 11 is not particularly limited, but examples thereof include a polyolefin-based resin such as polyethylene, polypropylene, or the like, a laminated nonwoven fabric obtained by stacking a nonwoven fabric on a polyethylene sheet, and a nonwoven fabric in which a waterproof film is interposed to substantially secure a liquid impervious property (in this case, the waterproof film and the nonwoven fabric form a liquid impervious sheet). Of course, in addition to these materials, a liquid impervious and moisture permeable material that has been favorably used from a viewpoint of preventing stuffiness in recent years can be used, for example. Examples of a sheet of the liquid impervious and moisture permeable material include a microporous sheet obtained by kneading an inorganic filler in a polyolefin-based resin such as polyethylene or polypropylene, molding a sheet, and then stretching the sheet in a monoaxial or biaxial direction. Furthermore, a nonwoven fabric using a micro denier fiber, a nonwoven fabric that has reinforced leakproofness by reducing a space between fibers by applying heat and pressure, and a sheet that has become liquid impervious without using a waterproof film by a method for applying a super absorbent polymer, a hydrophobic resin, or a water repellent agent can be used as the liquid impervious sheet 11.

The liquid impervious sheet 11 in the illustrated example is slightly wider than the top sheet 30 and narrower than the outer sheet 12, but is not limited thereto. An appropriate modification can be made, for example, the liquid impervious sheet 11 has the same width as the outer sheet 12.

(Top Sheet)

As the top sheet 30, a liquid pervious sheet, for example, a perforated or imperforated nonwoven fabric or a porous plastic sheet can be used. The nonwoven fabric is not particularly limited concerning a raw material fiber thereof. Examples thereof include a synthetic fiber such as a polyolefin-based fiber including polyethylene and polypropylene, a polyester-based fiber, or a polyamide-based fiber, a regenerated fiber such as rayon or cupra, a natural fiber such as cotton, and a mixed fiber and a composite fiber in which two or more kinds of these fibers are used. Furthermore, the nonwoven fabric may be manufactured by any processing. Examples of a processing method include a known method such as a spunlacing method, a spunbonding method, a thermal bond method, a melt blown method, a needle punching method, an air through method, and a point bond method. For example, if flexibility and drapeability are demanded, a spunlacing method is a preferable processing method. If bulkiness and softness are demanded, a thermal bond method is a preferable processing method.

The top sheet 30 may be formed of a single sheet or a stacked sheet obtained by bonding two or more sheets to each other. Similarly, the top sheet 30 may be formed of one sheet or two or more sheets in a plane direction.

The top sheet 30 in the illustrated example extends to a lateral side of a side edge of the absorber 56, but is not limited to thereto, and may extend to a side edge of the outer sheet 12. In an embodiment having a rising gather, an appropriate modification can be made, for example, the top sheet 30 may extend only up to a width direction inside of the side edge of the absorber as long as extending up to a root portion of the rising gather.

(Intermediate Sheet)

In order to move excrement that has passed through the top sheet 30 to the absorber to prevent returning, it is possible to dispose the intermediate sheet (also referred to as "second sheet") 40 between the top sheet 30 and the absorbent element 50. This intermediate sheet 40 not only quickly transfers excrement to the absorber to enhance absorption performance by the absorber, but also prevents returning of the absorbed excrement from the absorber, and improves a texture of a surface of the top sheet 30. The intermediate sheet 40 can be omitted.

A material of the intermediate sheet 40 is not particularly limited, and for example, a similar material to that of the top sheet 30 can be used. The intermediate sheet 40 is preferably bonded to the top sheet 30. In a case where heat embossing or ultrasonic welding is used for the bonding, a material of the intermediate sheet 40 preferably has approximately the same melting point as the top sheet 30. In addition, if transmission of a solid content in stool is considered, fibers used for the intermediate sheet 40 preferably have a fineness of 5.0 to 7.0 dtex, but a liquid residue in the top sheet 30 is increased. Meanwhile, when the fineness of fibers used for the intermediate sheet 40 is 1.0 to 2.0 dtex, a liquid residue of the top sheet 30 is unlikely to be generated, but a solid content in stool is unlikely to pass therethrough. Therefore, fibers of a nonwoven fabric used for the intermediate sheet 40 preferably have a fineness of about 2.0 to 5.0 dtex. Note that the intermediate sheet 40 can be a mesh film or the like obtained by forming many pores in a film material such as polyethylene.

The intermediate sheet 40 in the illustrated embodiment is disposed at the center so as to be shorter than the width of the absorbent element 50, but may be disposed over the maximum width. The longitudinal length of the intermediate sheet 40 may be the same as the maximum length of the diaper, may be the same as the length of the absorbent element 50, or may be within a short length range centered on a liquid receiving region.

(Absorbent Element)

The absorbent element 50 is a portion for absorbing and holding a liquid such as urine or loose stool, and includes the absorber 56 and the wrapping sheet 58 wrapping the entire absorber 56 in the illustrated example. For example, in a case where the absorber 56 has excellent shape maintainability, the wrapping sheet 58 can be omitted as necessary. In this case, the absorbent element 50 includes only the absorber 56. The absorbent element 50 can be bonded to an inner surface of the liquid impervious sheet 11 via an adhesive such as a hot melt adhesive on a back surface thereof.

(Absorber)

The absorber 56 can be formed of an assembly of fibers. As this fiber assembly, in addition to those obtained by accumulating short fibers such as fluff pulps or synthetic fibers, a filament assembly obtained by opening a tow (fiber bundle) of synthetic fibers such as cellulose acetate as necessary can also be used. In a case where fluff pulps or short fibers are accumulated, a fiber basis weight may be, for example, about 100 to 300 g/m$^2$. In a case of a filament assembly, a fiber basis weight may be, for example, about 30 to 120 g/m$^2$. In a case of a synthetic fiber, a fineness is, for example, 1 to 16 dtex, preferably 1 to 10 dtex, and more preferably 1 to 5 dtex. In a case of a filament assembly, the filament may be formed of non-crimped fibers but is preferably formed of crimped fibers. The degree of crimp of the crimped fibers may be, for example, about 5 to 75, preferably 10 to 50, and more preferably 15 to 50 per 2.54 cm. In addition, a uniformly crimped fiber can be used. In the absorber 56, super absorbent polymer particles are preferably dispersed and held.

In addition to such a rectangular shape as in the illustrated example, the absorber 56 preferably has an hourglass shape having a narrower portion with a narrower width than the front and back sides thereof in an intermediate portion in a front-back direction because fitting around a leg is improved.

The size of the absorber 56 can be determined appropriately as long as the absorber 56 extends to the front, back, left, and right of a ureteral port position. However, the absorber 56 preferably extends to the vicinity of peripheral edges of the main body 10 in the front-back direction LD and the width direction WD. Note that a reference numeral 56X represents the maximum width of the absorber 56, a reference numeral 10X represents the maximum length of the main body 10, and a reference numeral 10L represents the maximum length of the main body 10 (equal to the maximum length of the diaper in the illustrated embodiment).

(Super Absorbent Polymer Particles)

The absorber 56 may contain super absorbent polymer particles partially or entirely. The super absorbent polymer particles include "powder" in addition to "particles". As super absorbent polymer particles 54, those used for this type of absorbent article can be used as they are. The particle diameters of the super absorbent polymer particles are not particularly limited. However, for example, when sieving using a standard sieve of 500 μm (JIS Z8801-1: 2006) (shake for five minutes) is performed, and particles falling under the sieve using this sieving are sieved using a standard sieve of 180 μm (JIS Z8801-1: 2006) (shake for five minutes), it is desirable that a ratio of particles remaining on the standard sieve of 500 μm is 30% by weight or less, and a ratio of particles remaining on the standard sieve of 180 μm is 60% by weight or more.

A material of the super absorbent polymer particles can be used without particular limitation, but those having a water absorption capacity of 40 g/g or more are preferable. Examples of the super absorbent polymer particles include a starch-based material, a cellulose-based material, and a synthetic polymer-based material. A starch-acrylic acid (salt) graft copolymer, a saponified product of a starch-acrylonitrile copolymer, a cross-linked product of sodium carboxymethyl cellulose, an acrylic acid (salt) polymer, or the like can be used. As the shapes of the super absorbent polymer particles, a usually used particulate material shape is suitable, but other shapes can also be used.

As the super absorbent polymer particles, those having a water absorption rate of 70 seconds or less, particularly 40 seconds or less are suitably used. When the water absorption rate is too slow, so-called returning that a liquid supplied into the absorber 56 returns out of the absorber 56 tends to occur.

As the super absorbent polymer particles, those having a gel strength of 1000 Pa or more are suitably used. This makes it possible to effectively suppress sticky feeling after liquid absorption even in a case of using the bulky absorber 56.

The basis weight of the super absorbent polymer particles can be appropriately determined depending on the absorption amount required for an application of the absorber 56. Therefore, the basis weight can be 50 to 350 g/m$^2$ although this cannot be applied generally. The basis weight of a polymer of less than 50 g/m$^2$ makes it difficult to secure the absorption amount. The basis weight of more than 350 g/m$^2$ saturates an effect.

(Wrapping Sheet)

In a case where the wrapping sheet 58 is used, as a material thereof, tissue paper, particularly, crepe paper, a nonwoven fabric, a polylaminated nonwoven fabric, or a sheet with small holes can be used. However, it is desirable that the wrapping sheet 58 is a sheet from which super absorbent polymer particles do not escape. In a case where a nonwoven fabric is used instead of crepe paper, a hydrophilic SMS nonwoven fabric (SMS, SSMMS, or the like) is particularly suitable, and polypropylene, a polyethylene/polypropylene composite material, or the like can be used as a material thereof. A nonwoven fabric having a basis weight of 5 to 40 g/m$^2$, particularly of 10 to 30 g/m$^2$ is desirable.

A wrapping form of the wrapping sheet 58 can be determined appropriately. However, an embodiment is preferable in which the wrapping sheet 58 is wound around the absorber 56 cylindrically so as to surround front and back surfaces and both side surfaces of the absorber 56, the front and back end portions of the wrapping sheet 58 are caused to project from the front and back of the absorber 56, and a wound and overlapping portion and an overlapping portion of the front and back projecting portions are bonded by a bonding means such as a hot melt adhesive or material welding from viewpoints of ease of manufacture, prevention of leakage of the super absorbent polymer particles from front and back edges, and the like.

(Side Gather)

Figure 2:
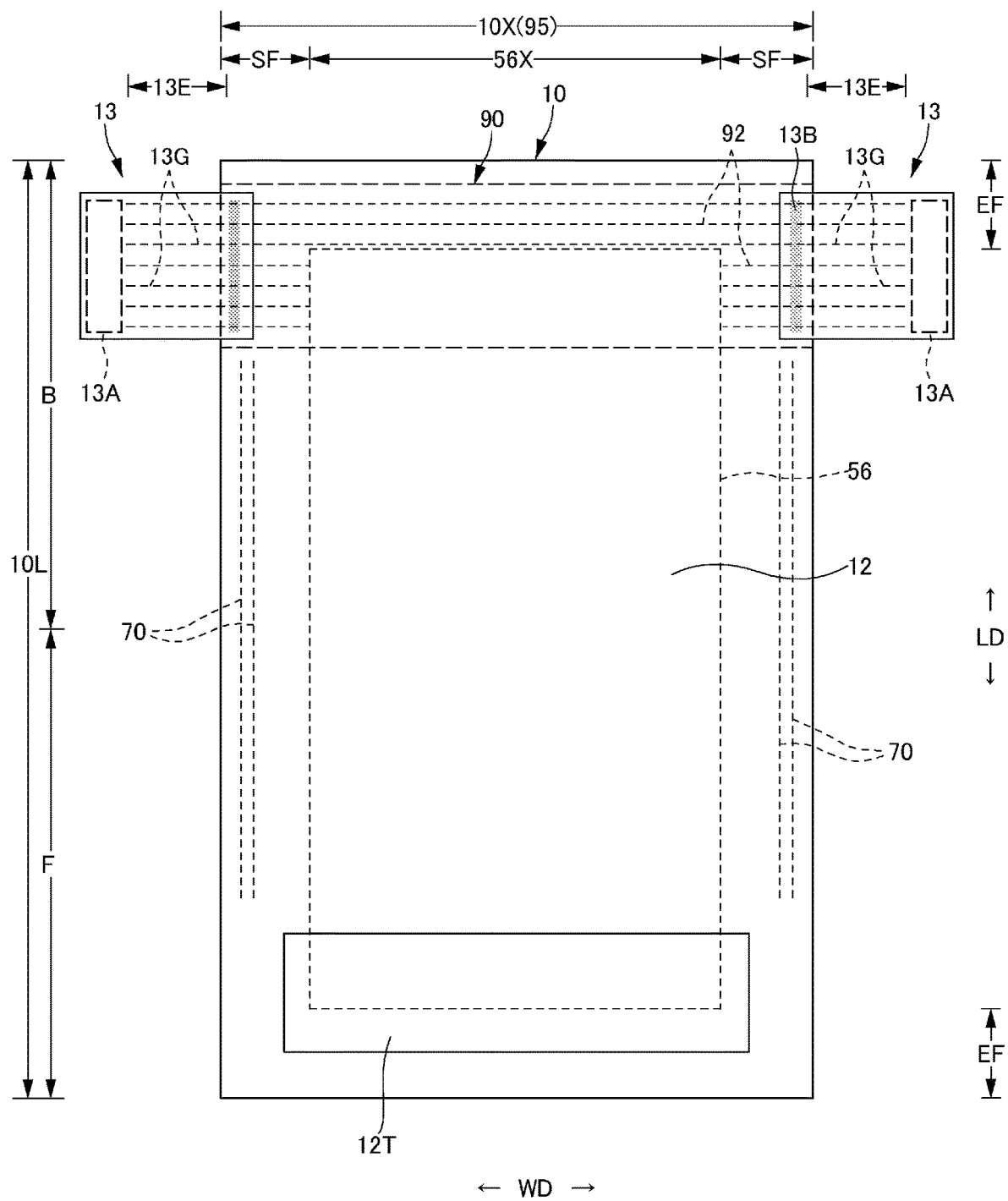
FIG. 2 is a plan view illustrating an outer surface of a tape-type disposable diaper in a state where the diaper is unfolded.
Figure 3:
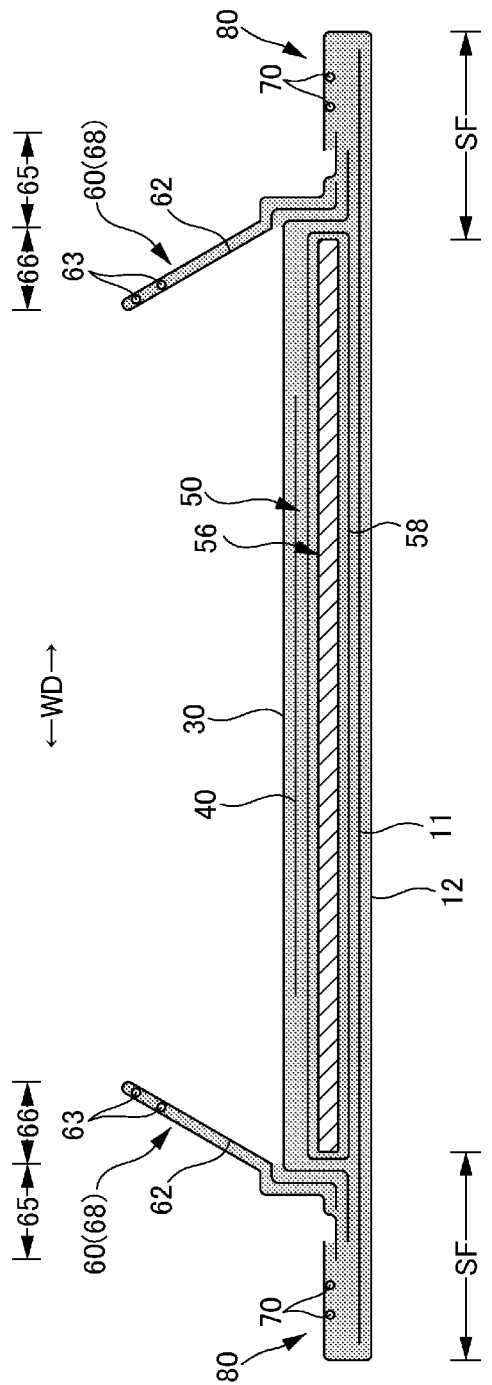
FIG. 3 is a 5-5 cross-sectional view of FIG. 1.
Figure 4:
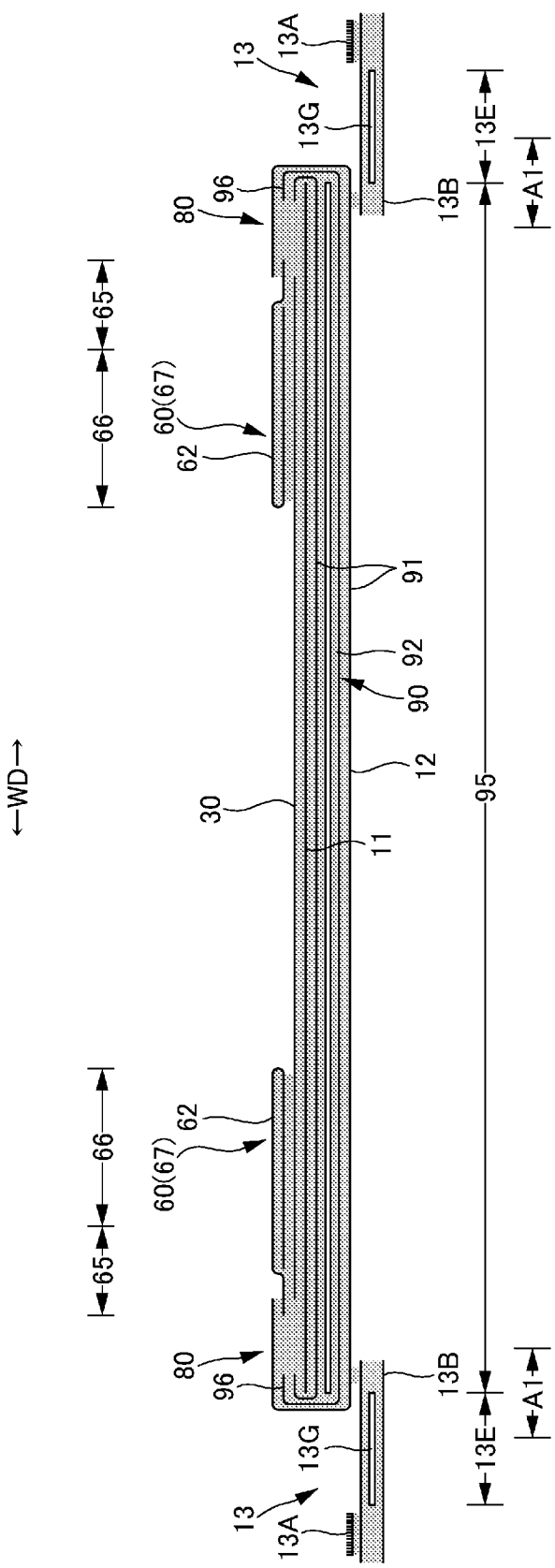
FIG. 4 is a 6-6 cross-sectional view of FIG. 1.
Figure 7:
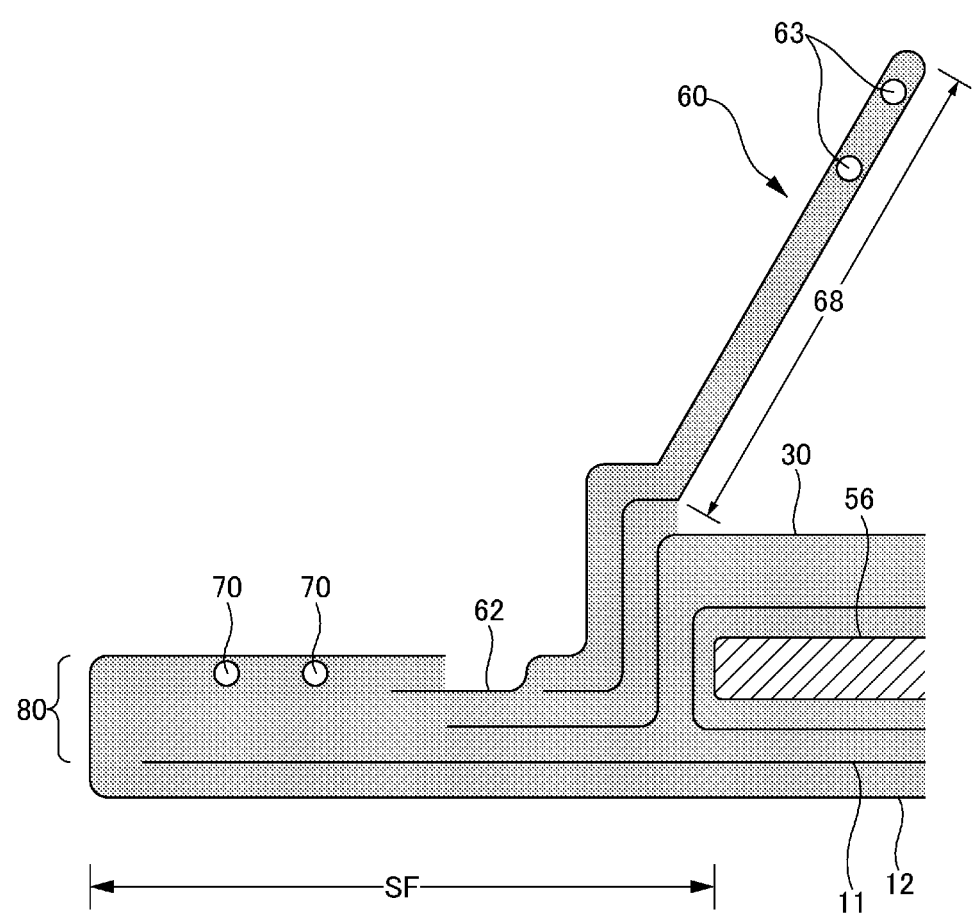
FIG. 7 is an enlarged cross-sectional view of a main part of a side gather portion.

As illustrated in FIGS. 2, 3, and 7, in order to improve fitting around a leg located in an intermediate portion of a side of the main body 10 in the front-back direction LD, a side elastic member 70 extending in the front-back direction LD is disposed between sheet layers in an intermediate portion of the side flap portion SF in the front-back direction LD (in the illustrated example, between the outer sheet 12 of a folded-back portion 80 described later and the liquid impervious sheet 11 or between the gather sheet 62 and the liquid impervious sheet 11). Due to expansion and contraction of the side elastic member 70, a portion having the side elastic member 70 (that is, in the illustrated example, the folded-back portion 80 described later) expands and contracts in the front-back direction LD.

(Rising Gather)

In order to block urine or loose stool moving laterally on the top sheet 30 to prevent side leakage, on both sides of a surface of the disposable diaper in the width direction WD, the rising gather 60 rising (protruding) from a side of the top sheet 30 to a skin side is disposed over the entire front-back direction.

In the illustrated example, the rising gather 60 includes: a root portion 65 fixed to a region including each of the side flap portions SF; a protruding portion 66 extending from the root portion 65; a fallen portion 67 in which both end portions of the protruding portion in a front-back direction are fixed in a fallen state; a non-fixed rising portion 68 located between front and back fallen portions in the protruding portion 66; and a gather elastic member 63 fixed in a state of being stretched in the front-back direction at least at a tip portion of the rising portion 68. The rising gather 60 is formed of a gather sheet 62 folded back at a tip. As the gather sheet 62, a water repellent nonwoven fabric can be used. As the gather elastic member 63, an elongated elastic member such as a rubber thread can be used. As illustrated in FIGS. 1 and 2, a plurality of the gather elastic members 63 may be disposed at intervals, or one gather elastic member 63 may be disposed. The stretch rate of a portion having the gather elastic member 63 is not particularly limited, but in a usual case, is preferably 150 to 350%, and more preferably 200 to 300%.

The root portion 65 of the rising gather 60 in the illustrated example is disposed only in the side flap portion SF, and is bonded to a side of the liquid impervious sheet 11 and a side of the outer sheet 12, but may extend from the side flap portion SF to a side of a region overlapping with the absorber 56.

Both ends of the protruding portion 66 of the rising gather 60 in the front-back direction LD are fallen portions. However, a portion therebetween is the non-fixed rising portions 68, and the rising portion 68 rises by a contraction force of the gather elastic member 63. At the time of wearing the diaper, the diaper is attached to a body in a boat shape, and a contraction force of the gather elastic member 63 acts. Therefore, the rising gather 60 rises and elastically adheres to a periphery of a leg by the contraction force of the gather elastic member 63. As a result, so-called side leakage from a periphery of a leg is prevented.

(Waist Stretching Sheet)

A belt-shaped waist stretching sheet 90 extending across the left and right side flap portions SF is disposed between both the fastening tapes 13, and the dorsal side portion B elastically expands and contracts in the width direction WD. Both ends of the waist stretching sheet 90 in the width direction WD are non-stretchable regions 96, and a portion between the non-stretchable regions 96 is a main body stretchable region 95 that expands and contracts in the width direction WD. The waist stretching sheet 90 may be located only at the end flap portion EF. However, the waist stretching sheet 90 is preferably disposed so as to extend from the end flap portion EF to a back end portion of the absorber 56 as in the illustrated example because the back end portion of the absorber 56 is firmly pressed against a body.

Figure 6:
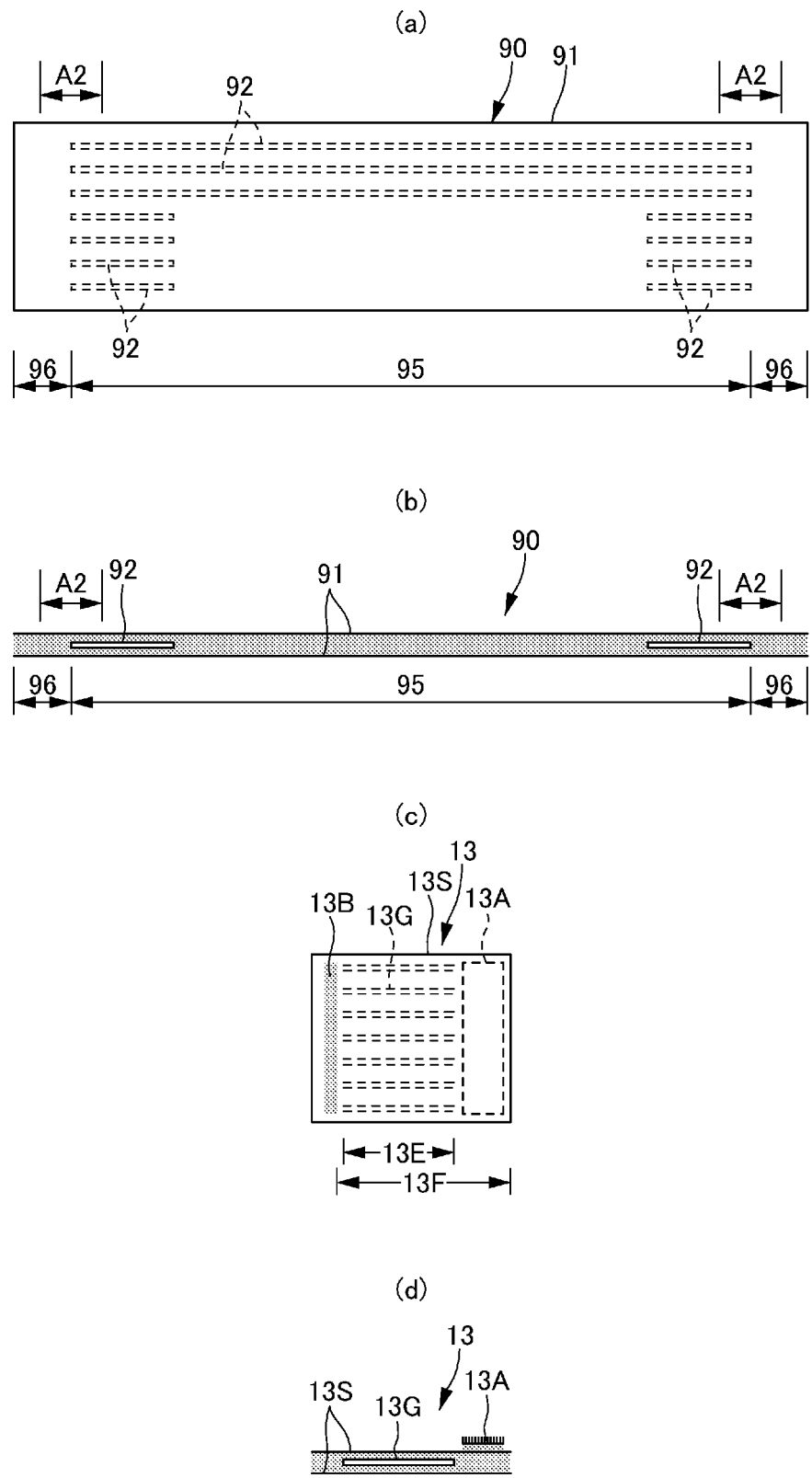
FIG. 6(a) is a plan view of a waist stretching sheet.
FIG. 6(b) is a cross-sectional view of the waist stretching sheet, FIG. 6(c) a plan view of a fastening tape.
FIG. 6(d) is a cross-sectional view of the fastening tape.

As the waist stretching sheet 90, a sheet-shaped elastic member such as a rubber sheet may be used, but a nonwoven fabric is preferably used from a viewpoint of air permeability. In this case, a sheet-shaped elastic member having air permeability such as an elastic nonwoven fabric can be used. However, as illustrated in FIG. 6, a member obtained by bonding two sheet layers 91 formed of a nonwoven fabric or the like with an adhesive such as a hot melt adhesive and fixing an elastic member 92 in a perforated sheet shape, a net shape, an elongated shape (a thread shape, a string shape, or the like), or the like between the sheet layers 91 in a stretched state in the width direction WD is suitably used. As a material of the sheet layer 91 in this case, a similar material to that of the outer sheet 12 can be used. The elastic member 92 preferably has a stretch rate of about 150 to 250%. In a case where an elongated (thread-shaped, string-shaped, or the like) member is used as the elastic member 92, it is preferable to dispose about 5 to 15 members each having a thickness of 420 to 1120 dtex at an interval of 3 to 10 mm in a front-back direction.

The sizes of the main body stretchable region 95 and the non-stretchable region 96 in the waist stretching sheet 90 can be determined appropriately. However, the width of the main body stretchable region 95 is preferably 70 to 100% of the width between the connecting portions 13A of the left and right fastening tapes 13 described later. The width of the non-stretchable region 96 is preferably about 5 to 40 mm in order to prevent contraction or curling at the time of being attached to the main body 10. The non-stretchable region 96 may be a region not having the elastic member 92. However, as described in Patent Literature 3, by attaching the elastic member 92 over the main body stretchable region 95 and the non-stretchable region 96 and cutting the elastic member 92 in the non-stretchable region 96, for example, a structure in which the elastic member 92 remains in the non-stretchable region 96 but hardly or never stretches may be formed.

A part of the elastic member 92 may be disposed so as to cross the absorber 56. However, as illustrated in FIG. 6, by cutting a part or the whole of a portion where the elastic member 92 overlaps with the absorber 56, for example, if a structure in which the elastic member 92 remains but hardly or never stretches is formed, a back end portion of the absorber 56 does not contract in the width direction. Therefore, fitting is further improved.

The waist stretching sheet 90 is disposed between the liquid impervious sheet 11 and the outer sheet 12 in the illustrated embodiment, but is not particularly limited to this disposition. For example, the waist stretching sheet 90 may be disposed between the liquid impervious sheet 11 and the absorbent element 50 or may be disposed outside the outer sheet 12. In a case where the outer sheet 12 is formed by stacking a plurality of sheet layers, the entire waist stretching sheet 90 may be disposed between the sheet layers of the outer sheet 12.

(Fastening Tape)

The fastening tapes 13 protrude from both sides of a lower torso portion of the dorsal side portion B, and each have a base portion 13B attached to the lower torso portion of the dorsal side portion B, a non-fixed fastener free portion 13F extending from the base portion 13B on a lateral side, and a connecting portion 13A to be detachably connected to an outer surface of the ventral side portion F, disposed at a tip portion pf the fastener free portion 13F.

As the connecting portion 13A of each of the fastening tapes 13, a hook material (hook member) of a mechanical fastener (hook and loop fastener) or an adhesive layer may be disposed. The hook material has many engaging projections on a connecting surface thereof. Examples of the shapes of the engaging projections include (A) tick shape, (B) J shape, (C) mushroom shape, (D) T shape, and (E) double J shape (a shape in which the J-shaped ones are connected to each other back to back), but any shape may be used. At the time of attaching the diaper, in a state where the side flap portion SF of the dorsal side portion B is superimposed on an outer side of the side flap portion SF of the ventral side portion F, the connecting portion 13A of the fastening tape 13 is connected to an appropriate position on an outer surface of the ventral side portion F.

As the fastening tape 13, it is possible to adopt not only a stretching type (side panel type) having a tape stretchable region 13E in which at least a portion between the base portion 13B and the connecting portion 13A expands and contracts in the width direction WD as illustrated in FIGS. 6(c), 6(d), and 12 but also a non-stretching type (tab type) having no tape stretchable region as illustrated in FIG. 19.

The stretch rate of the tape stretchable region 13E in the stretching type fastening tape 13 is not particularly limited, but is preferably about 150 to 250%. The structure of the tape stretchable region 13E is not particularly limited. For example, at least an elastic stretchable portion of the fastening tape 13 can be formed using a sheet having elasticity by itself, such as a rubber sheet or a stretchable nonwoven fabric. As illustrated in FIGS. 6(c), 6(d), and 12, it is also suitable to form at least the tape stretchable region 13E of the fastening tape 13 using one obtained by bonding two sheet layers 13S formed of a nonwoven fabric or the like with an adhesive such as a hot melt adhesive and fixing an elastic member 13G in a perforated sheet shape, a net shape, an elongated shape (a thread shape, a string shape, or the like), or the like between the sheet layers 13S in a stretched state in the width direction WD. As described above, a product obtained by attaching the plurality of elongated elastic members 13G to the sheet layer 13S at intervals is widely used in the technical field of the disposable diaper, and therefore is easily manufactured. Furthermore, by making the thickness of the elongated elastic member 13G, the number thereof, the stretch rate thereof, the interval thereof, and the type of a material thereof different, a contraction property of the fastening tape 13 can be easily adjusted advantageously. As a material of the sheet layer 13S in this case, a similar material to that of the outer sheet 12 can be used. In a case where an elongated (thread-shaped, string-shaped, or the like) member is used as the elastic member 13G, it is possible to dispose about 5 to 15 members each having a thickness of 420 to 1120 dtex at an interval of 3 to 10 mm in a front-back direction.

The tape stretchable region 13E may be disposed over the entire fastening tape 13 in the width direction WD (that is, including the base portion 13B and the connecting portion 13A) as long as being disposed at least in a portion between the base portion 13B and the connecting portion 13A. However, when the base portion 13B or the connecting portion 13A contracts, connection of the connecting portion 13A may be insufficient, or bonding failure of the base portion 13B may occur. Therefore, the tape stretchable region 13E is preferably disposed in a range of 70 to 100% of the width direction WD range between the base portion 13B and the connecting portion 13A. In this case, each of the base portion 13B and the connecting portion 13A may be a region not having the elastic member 13G. However, by attaching the elastic member 13G over the entire fastening tape 13 in the width direction WD and cutting the elastic member 13G at the base portion 13B and the connecting portion 13A, for example, a structure in which the elastic member 13G remains in the base portion 13B and the connecting portion 13A but hardly or never stretches may be formed.

The connecting portion 13A of the stretching type fastening tape 13 may be disposed in the sheet layer 13S constituting the tape stretchable region 13E as illustrated in FIGS. 6(c) and 6(d). However, as in the example illustrated in FIG. 12, preferably, a support piece 13C protruding from a tip of the tape stretchable region 13E is attached to a tip portion of the fastening tape 13, and the connecting portion 13A is disposed on the support piece 13C because manufacture is easy. It is desirable that the support piece 13C has the connecting portion 13A in an intermediate portion in the width direction WD, and a tip portion thereof is a tab part having no connecting portion 13A. The shape of the support piece 13C can be appropriately determined, and in the illustrated example, the length thereof in the front-back direction LD becomes shorter toward a tip, and a portion where the length in the front-back direction LD is short has the connecting portion 13A. However, the shape may also be a rectangular shape. In a case where the support piece 13C has a rectangular shape, the length thereof in the front-back direction LD is preferably shorter than the sheet layer 13S constituting the tape stretchable region 13E. As a material of the support piece 13C, a known material such as a nonwoven fabric, a plastic film, a polylaminated nonwoven fabric, paper, or a composite material thereof can be used without particular limitation. However, a spunbonded nonwoven fabric, an air through nonwoven fabric, or a spunlaced nonwoven fabric having a fineness of 1.0 to 3.5 dtex, a basis weight of 20 to 100 g/m$^2$, and a thickness of 1 mm is preferable.

The shape of the stretching type fastening tape 13 can be appropriately determined, and the tape stretchable region 13E preferably has a rectangular shape as in the illustrated example because manufacture is easy. However, the tape stretchable region 13E can have a trapezoidal shape in which the length thereof in the front-back direction LD becomes shorter toward a tip side. The size of the stretching type fastening tape 13 can be appropriately determined, but the length of the tape stretchable region 13E in the front-back direction LD is preferably about 20 to 100 mm, and the length of the tape stretchable region 13E in the width direction WD is preferably about 0 to 90 mm.

The structure of the non-stretching type fastening tape 13 is not particularly limited, and a known structure can be adopted. The non-stretching type fastening tape 13 in the illustrated example includes the support piece 13C protruding from a side edge of the main body 10 and the connecting portion 13A disposed on an intermediate portion of a portion protruding from the side edge of the main body 10 in the width direction WD in the support piece 13C. As a material of the support piece 13C, a material similar to that of the stretching type fastening tape can be used.

(Target Sheet)

A target sheet 12T having a target for facilitating connection is preferably disposed at a connecting location of the fastening tape 13 in the ventral side portion F. In a case where the connecting portion 13A is formed of a hook material, as the target sheet 12T, it is possible to use one in which many loop threads making engaging projections of the hook material entangled therewith are disposed on a surface of a sheet substrate formed of a plastic film or a nonwoven fabric. In a case of an adhesive layer, it is possible to use one obtained by subjecting a surface of a sheet substrate formed of a plastic film having a smooth surface with high pressure-sensitive adhesiveness to a peeling treatment. In a case where the connecting location of the fastening tape 13 in the ventral side portion F is formed of a nonwoven fabric, for example, when the outer sheet 12 in the illustrated embodiment is formed of a nonwoven fabric and the connecting portion 13A of the fastening tape 13 is formed of a hook material, the target sheet 12T can be omitted, and the hook material can be entangled with the nonwoven fabric of the outer sheet 12 to be connected. In this case, the target sheet 12T may be disposed between the outer sheet 12 and the liquid impervious sheet 11.

Folded-Back Portion)

Characteristically, the main body 10 has the folded-back portion 80 obtained by folding back a side including a portion having the non-stretchable region 96 of the waist stretching sheet 90 to a center side and fixing thereto. The fastening tape 13 is attached to the main body 10 such that a base edge of the tape stretchable region 13E is located within the range A1 of ±5 mm, more preferably within the range A1 of ±2 mm from a side edge of the main body stretchable region 95 in the width direction WD. As a result, the (unavoidably formed) width of the non-stretchable region 96 of the waist stretching sheet 90 occupied in the width of the main body 10 can be reduced. In addition, in a case where the fastening tape 13 has the tape stretchable region 13E, continuity of the stretchable region across the left and right fastening tapes 13 can be improved.

The base portion 13B of the fastening tape 13 may be connected to a position overlapping with the main body stretchable region 95 or may be disposed adjacent to a side edge of the main body stretchable region 95. Bonding between the base portion 13B of the fastening tape 13 and the main body 10 is preferably formed so as to be elongated in the front-back direction LD as in the illustrated example, and is preferably strong. Therefore, bonding is preferably performed by welding such as ultrasonic sealing or heat sealing, but may be performed with a hot melt adhesive. The folded-back portion 80 is disposed in a partial range of the side flap portion SF in the width direction WD, but may extend to the entire side flap portion SF in the width direction WD or to a center side of the side flap portion SF in the width direction WD.

The folded-back portion 80 may include an end portion of the main body stretchable region 95 or may include only a part of the non-stretchable region 96. That is, a folded-back position is preferably located at a boundary between the main body stretchable region 95 and the non-stretchable region 96. However, the folded-back position may be located at a center side of the boundary although not illustrated, or may be located outside the boundary as in the illustrated example. In a usual case, the folded-back position is preferably located within the range A2 of ±5 mm, more preferably within the range A2 of ±2 mm in the width direction WD based on the boundary between the main body stretchable region 95 and the non-stretchable region 96.

Figure 8:
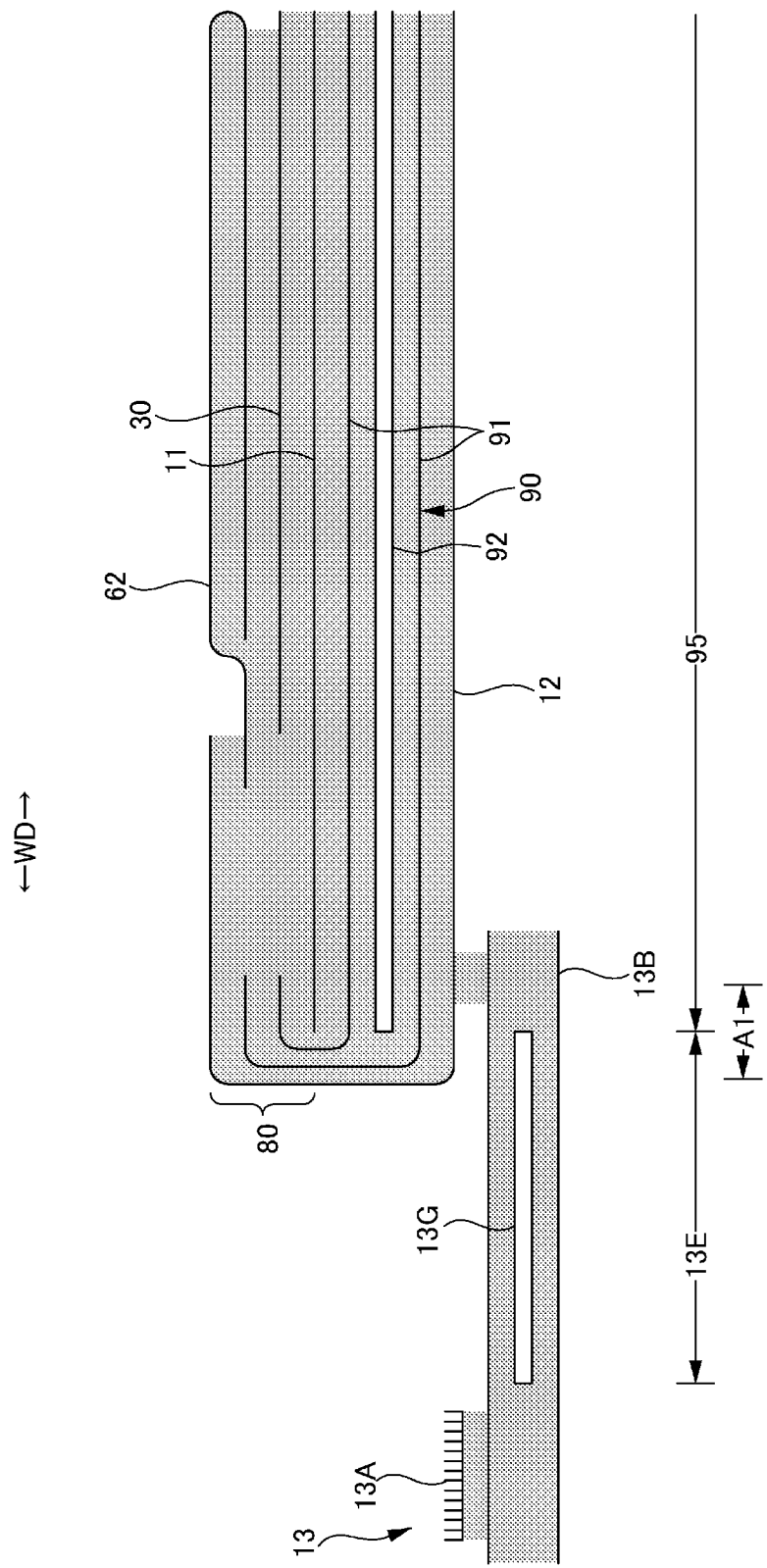
FIG. 8 is an enlarged cross-sectional view illustrating a portion having a waist stretching sheet and a fastening tape.

In a case where the folded-back portion 80 is formed simply by folding back a side of the main body 10, there are points to be considered, for example, the number of stacked material layers increases to make the folded-back portion 80 hard, the fastening tape 13 which is conventionally sandwiched between materials and is not exposed is exposed, and the outer sheet 12 placing importance on strength rather than flexibility becomes a skin side. Therefore, as a preferable embodiment, as in the examples illustrated in FIGS. 4 and 8, an embodiment is proposed in which the main body stretchable region 95 in the waist stretching sheet 90 extends across the left and right side flap portions SF, each of the side flap portions SF is a portion in which the gather sheet 62, the liquid impervious sheet 11, the waist stretching sheet 90, and the outer sheet 12 are stacked, the folded-back portion 80 is formed in each of the side flap portions SF and a portion obtained by folding back the gather sheet 62, at least a part of the non-stretchable region 96 of the waist stretching sheet 90, and the outer sheet 12 to a front surface side, and the base portion 13B of the fastening tape 13 is attached to a back surface of a portion having the folded-back portion 80 in each of the side flap portions SF.

When the folded-back portion 80 has such a structure, by attaching the base portion 13B of the fastening tape 13 to a back surface of a portion having the folded-back portion 80 in the side flap portion SF, not only the strength of a portion where a force is concentrated during use (a portion where the fastening tape 13 is attached) is high, but also no force to peel off the folded-back portion 80 is applied advantageously. Alternatively, by attaching no base portion 13B of the fastening tape 13 to a skin side, a texture of a surface on the skin side is not impaired.

Figure 9:
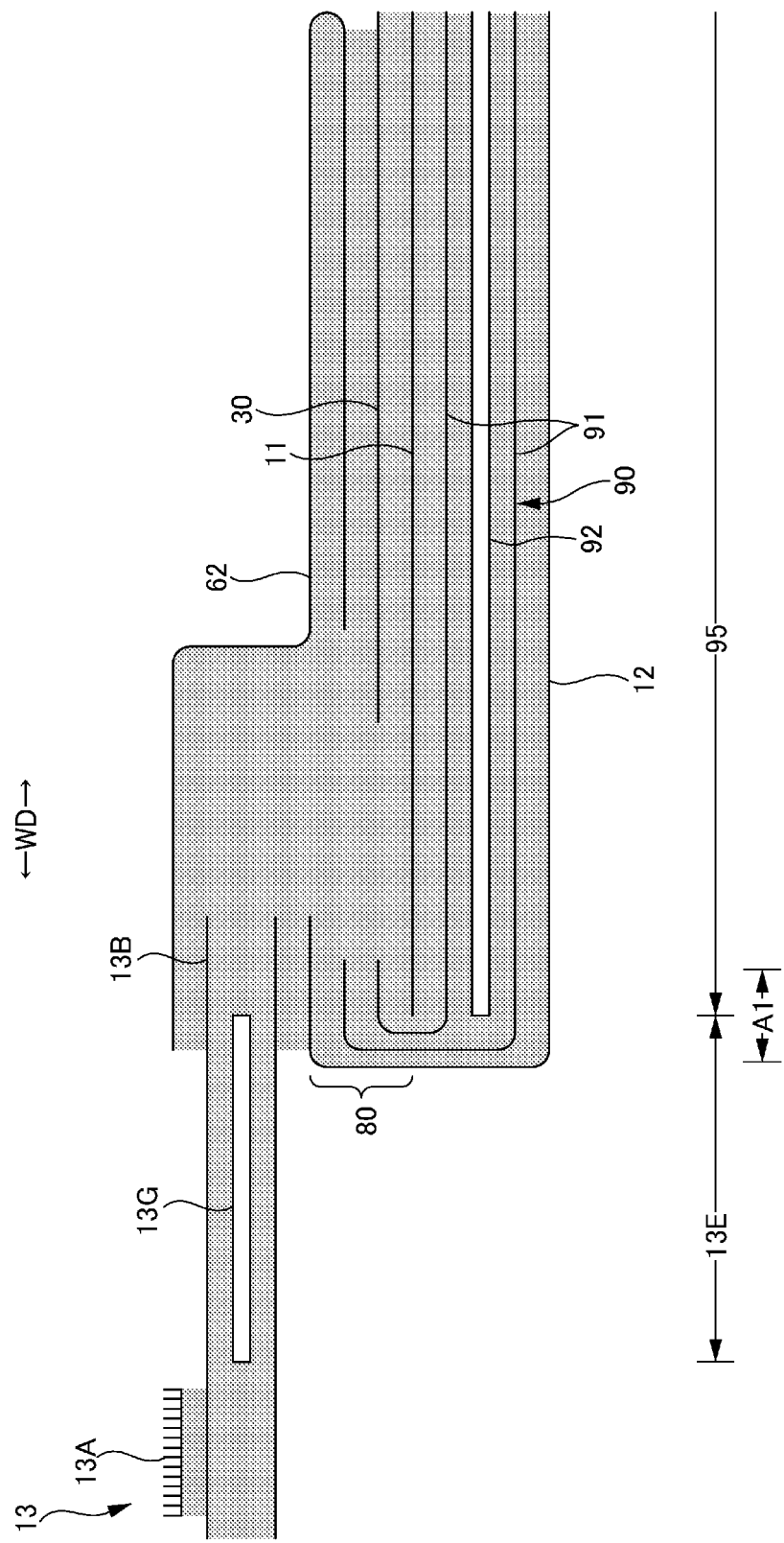
FIG. 9 is an enlarged cross-sectional view illustrating a portion having a waist stretching sheet and a fastening tape in another embodiment.

As illustrated in FIG. 9, an embodiment is also preferable in which the folded-back portion 80 is formed in the side flap portion SF and is a portion obtained by folding back at least a part of the non-stretchable region 96 of the waist stretching sheet 90 and the outer sheet 12 to a front surface side, a front surface side of the folded-back portion 80 is covered with a side of the gather sheet 62, and the base portion 13B of the fastening tape 13 is attached between the folded-back portion 80 in the side flap portion SF and the side of the gather sheet 62. In this case, by attaching the base portion 13B of the fastening tape 13 to the folded-back portion 80 of the side flap portion SF, the strength of a portion where a force is concentrated during use (attachment portion of the fastening tape 13 in the folded-back portion 80) is high. Alternatively, the base portion 13B of the fastening tape 13 is not exposed, and a hard material such as the outer sheet 12 is not exposed due to covering of the front surface side of the folded-back portion 80 with the side of the gather sheet 62. Therefore, a texture is not impaired.

Figure 10:
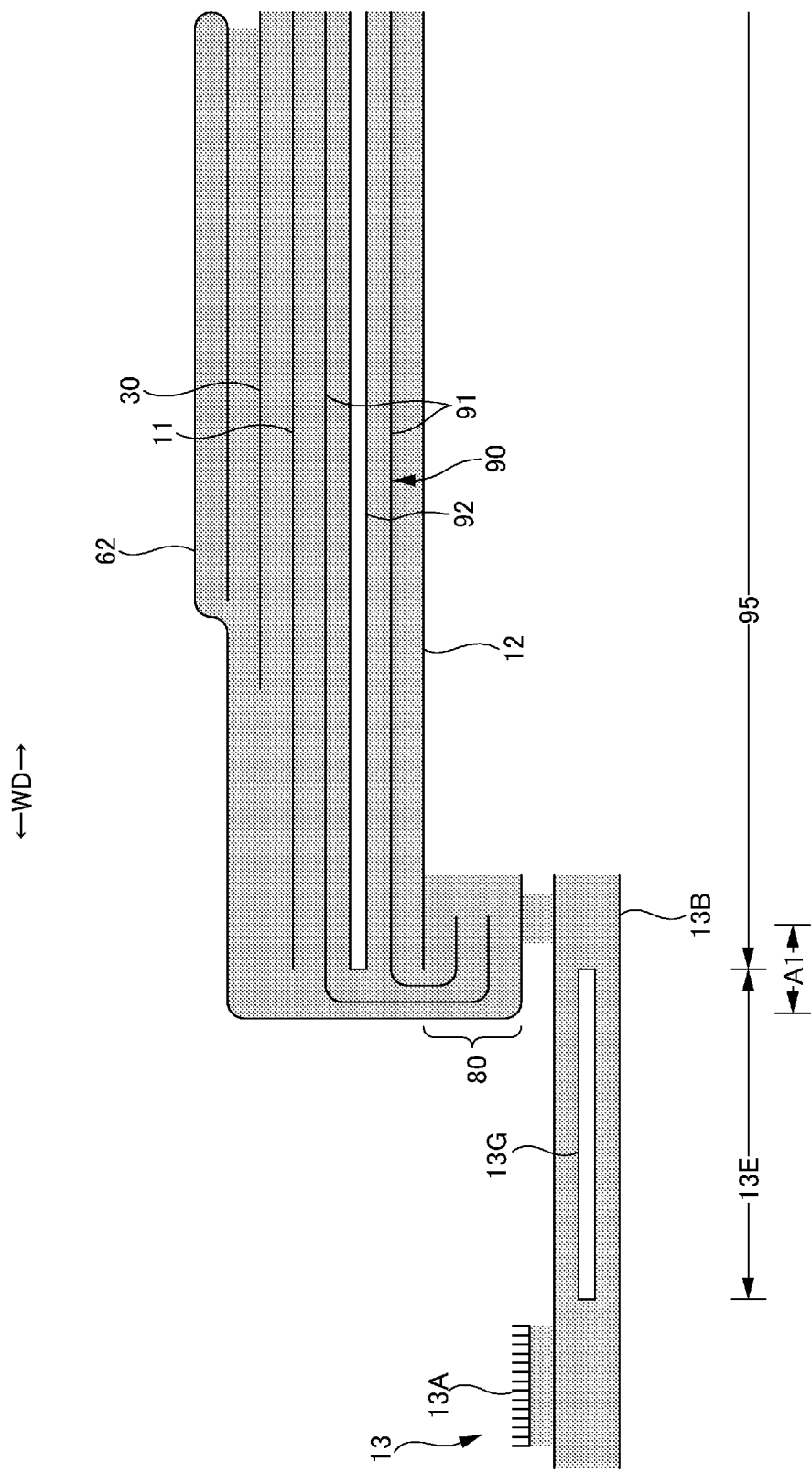
FIG. 10 is an enlarged cross-sectional view illustrating a portion having a waist stretching sheet and a fastening tape in another embodiment.
Figure 13:
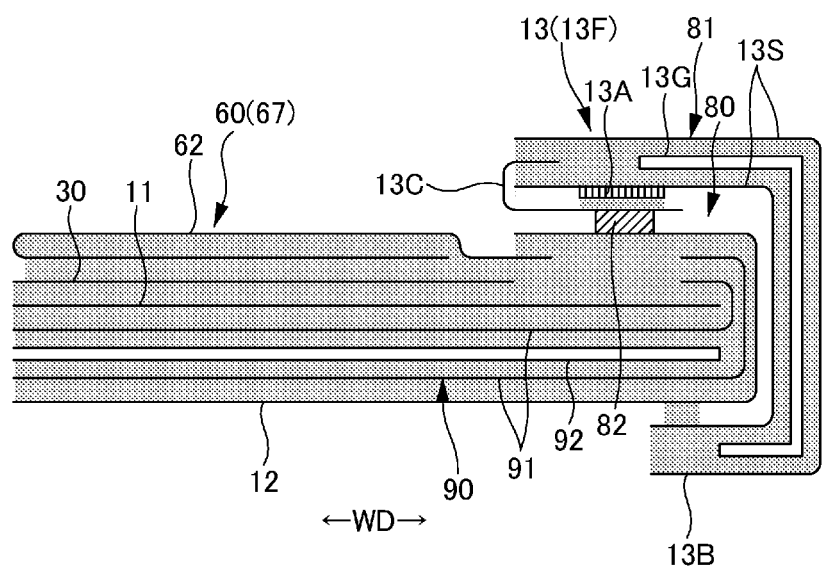
FIG. 13 is an enlarged cross-sectional view illustrating a portion having a waist stretching sheet and a fastening tape in another embodiment.
Figure 15:
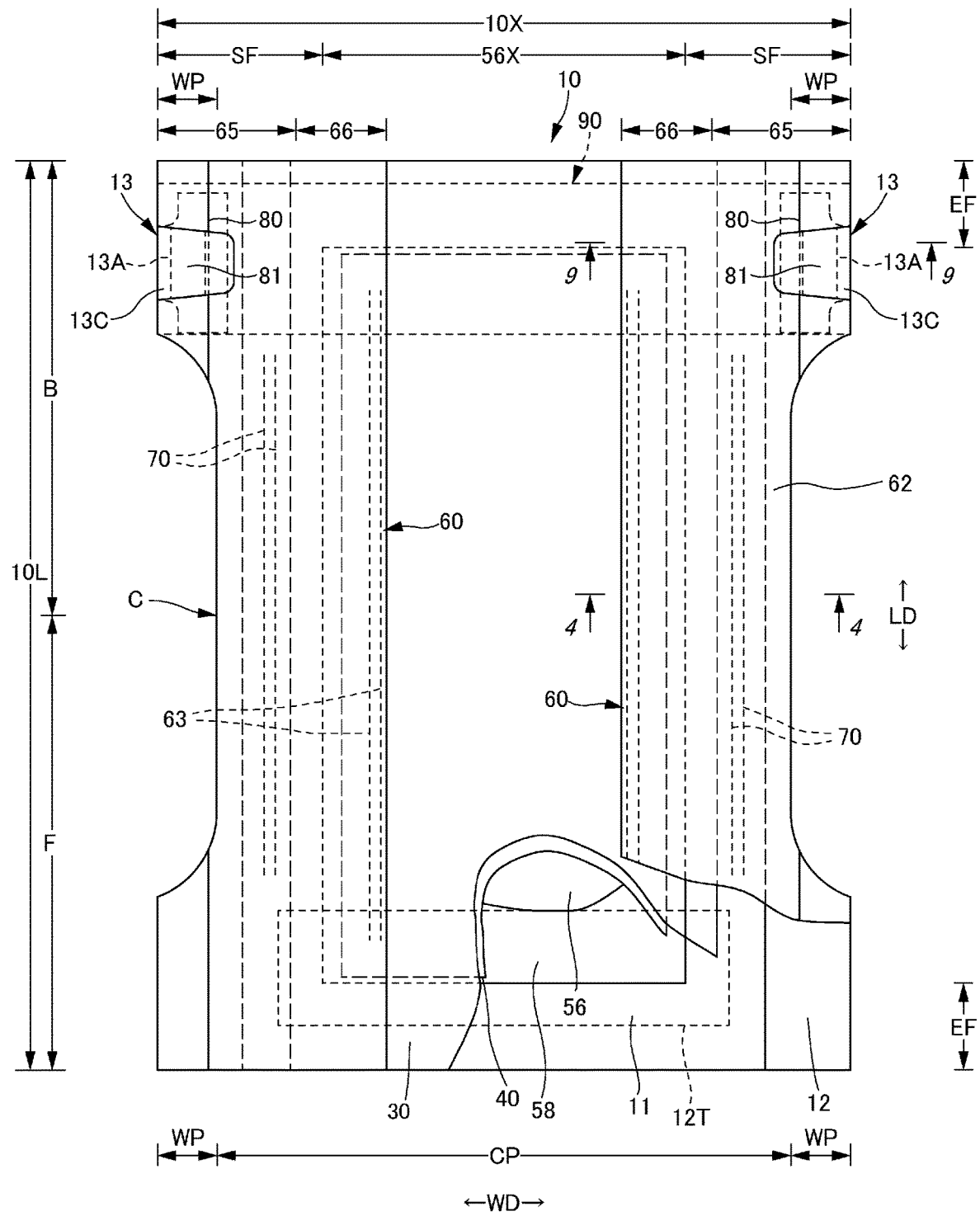
FIG. 15 is a plan view illustrating an inner surface of another tape-type disposable diaper in an unfolded state (fastener assembly is in a folded state).
Figure 16:
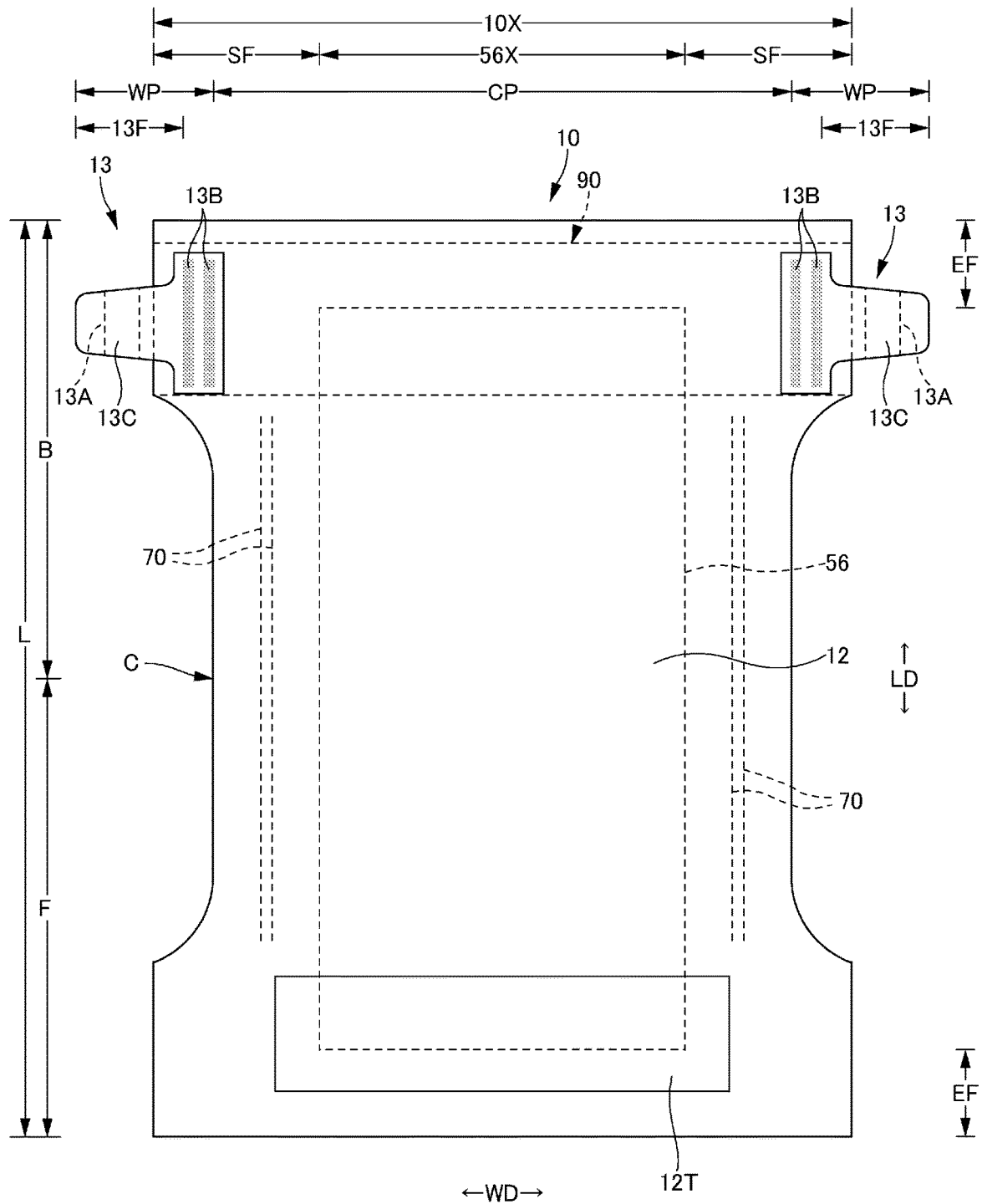
FIG. 16 is a plan view illustrating an outer surface of another tape-type disposable diaper in an unfolded state.
Figure 17:
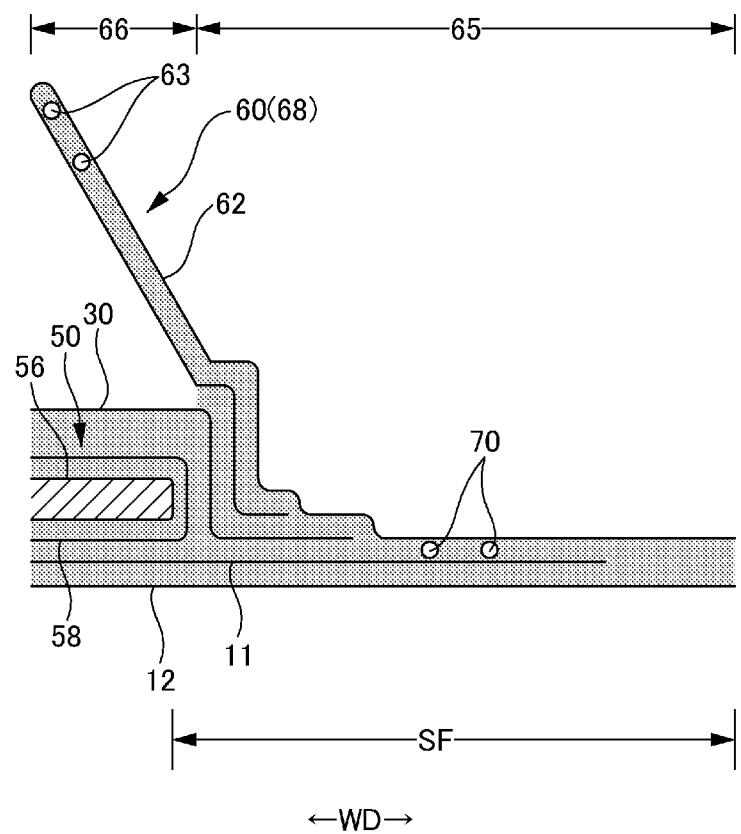
FIG. 17 is a 4-4 cross-sectional view of FIG. 15.
Figure 18:
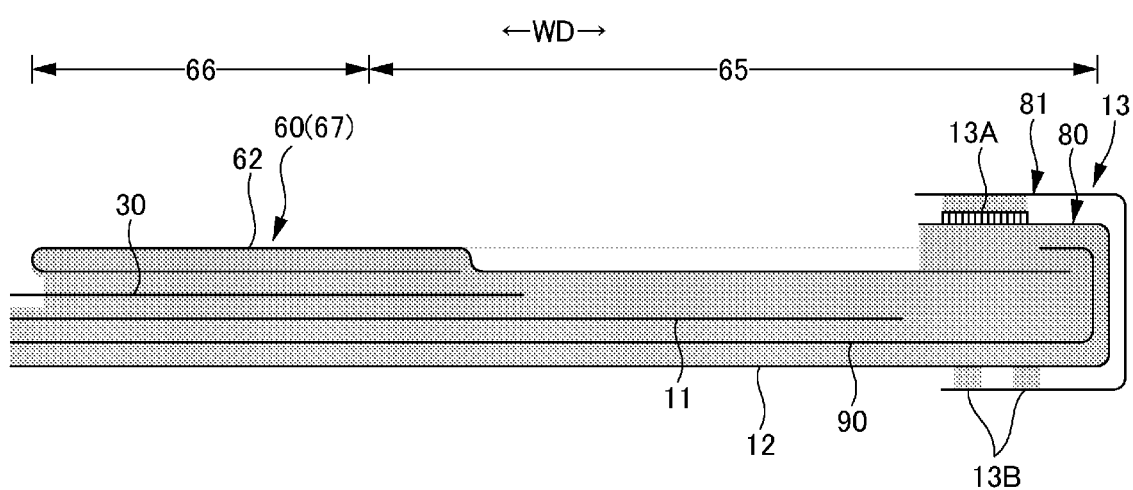
FIG. 18 is a 9-9 cross-sectional view of FIG. 15.

Furthermore, as illustrated in FIG. 10, an embodiment is also preferable in which the folded-back portion 80 is formed in the side flap portion SF and is a portion obtained by folding back the gather sheet 62, at least a part of the non-stretchable region 96 of the waist stretching sheet 90, and the outer sheet 12 to a back surface side, and the base portion 13B of the fastening tape 13 is attached to a back surface of a portion having the folded-back portion 80 in the side flap portion SF. In this case, by attaching the base portion 13B of the fastening tape 13 to the folded-back portion 80 of the side flap portion SF, the strength of a portion where a force is concentrated during use (attachment portion of the fastening tape 13 in the folded-back portion 80) is high. In addition, by forming the front surface side of the folded-back portion 80 with the gather sheet 62 and attaching no base portion 13B of the fastening tape 13 to a skin side, a texture of a surface on the skin side is not impaired.

Meanwhile, the folded-back portion 80 tends to increase a thickness thereof and to become hard. Therefore, all the sheets constituting the folded-back portion 80 may extend to a tip of the folded-back portion 80 (edge on a center side in the width direction WD). However, more preferably, some of the sheets extend only to an intermediate portion of the folded-back portion 80 in the width direction WD. For example, in the illustrated example, the outer sheet 12 extends to a tip of the folded-back portion 80, but the waist stretching sheet 90 extends only to the middle of the folded-back portion 80. Therefore, flexibility of the folded-back portion 80 is unlikely to be impaired.

As in the illustrated example, a structure is preferable in which the folded-back portion 80 does not include the liquid impervious sheet 11 that particularly tends to be hard from such a viewpoint. Furthermore, the folded-back portion 80 is preferably bonded to a sheet adjacent to a back surface side of the folded-back portion 80 of the main body 10 via a hot melt adhesive disposed in an intermittent pattern from a similar viewpoint (not illustrated).

In the above example, the side of the main body 10 is folded back in the width direction WD over the entire front-back direction LD, but only a part including the waist stretching sheet 90 may be folded back to form the folded-back portion 80.

(Fastener Folded-Back Portion)

As in the examples illustrated in FIGS. 11, 13, and 15 to 18, the fastener free portion 13F of the fastening tape 13 has a fastener folded-back portion 81 folded back to an upper side of the folded-back portion 80 of the main body 10 at a side edge of the main body 10. The fastener folded-back portion 81 is preferably fixed to the folded-back portion 80 temporarily at a portion overlapping with the folded-back portion 80. The base portion 13B of the fastening tape 13 may be disposed on the side flap portion SF as in the illustrated example, or may be disposed at a position overlapping with the absorber 56 although not illustrated.

An embodiment is preferable in which temporary fixing of the fastener folded-back portion 81 to the folded-back portion 80 of the main body 10 is performed by connecting the connecting portion 13A of the fastener folded-back portion 81 to the folded-back portion 80 as in the example illustrated in FIG. 11. As in the example illustrated in FIG. 13, a part or the whole of a portion where the folded-back portion 80 and the fastener folded-back portion 81 overlap with each other can be releasably and temporarily fixed with a hot melt adhesive 82 (or by welding) without using the connecting portion 13A. As in the illustrated example, this method is suitable for an embodiment in which a tip portion of the fastening tape 13 is folded back and the folded-back portion is temporarily fixed to the fastening tape 13 itself by the connecting portion 13A.

Figure 20:
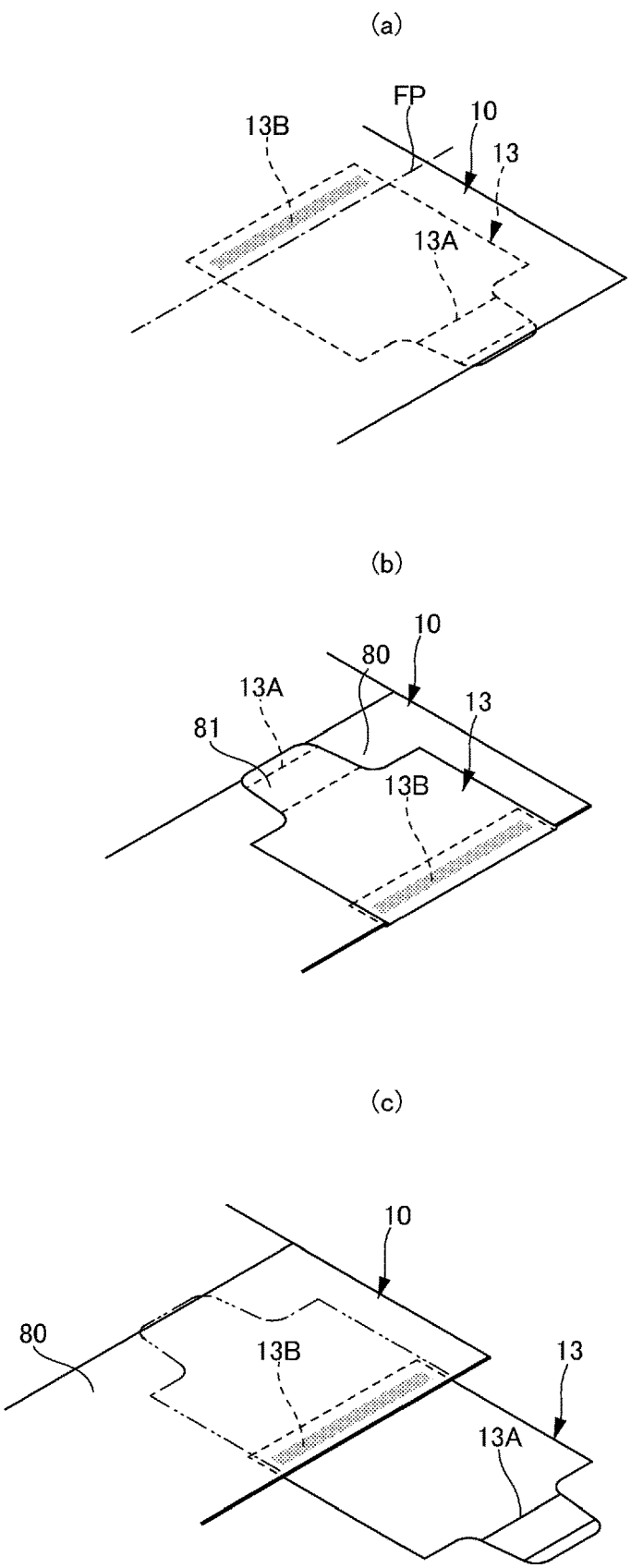
FIG. 20(a), FIG. 20(b), and FIG. 20(c) are enlarged perspective views of a main part, illustrating a step of assembling a fastener assembly, a step of folding back a fastener assembly, and a state of use, respectively.

Such a structure can be manufactured, at the time of manufacture, by disposing the fastening tape 13 such that a site serving as the base portion 13B of the fastening tape 13 is located at a site serving as a back surface side of the main body 10 and extends to a site serving as the folded-back portion 80 in a state before the folded-back portion 80 of the main body 10 is formed as illustrated in FIG. 20(a), fixing the site serving as the base portion 13B to the main body 10, releasably and temporarily fixing the fastening tape 13 to the site serving as the folded-back portion 80, and then folding back both side portions of the main body 10 and the fastening tape 13 integrally at a folding position FP along a side edge of the main body 10 as illustrated in FIG. 20(b) to form the folded-back portion 80 and the fastener folded-back portion 81. That is, at the time of folding-back, the fastening tape 13 is integrated with the main body 10 at two places of the base portion 13B and the temporarily fixed portion. Therefore, folding back of the fastening tape 13 is unlikely to be unsuitable unlike in prior art. As a result, according to the present aspect, it is possible to effectively prevent positional deviation of the folded-back portion of the fastening tape 13. Incidentally, the fastener folded-back portion 81 in the fastening tape 13 is only temporarily fixed to the folded-back portion 80 of the main body 10. Therefore, at the time of use, by releasing the temporary fixing by unfolding the fastener folded-back portion 81 to a lateral side as illustrated in FIG. 20(c), a portion having the connecting portion 13A in the fastening tape 13 protrudes from a side edge of the folded-back portion 80 of the main body 10. The diaper according to the present aspect can be used similarly to a conventional one except for inclusion of the folded-back portion 80 in the main body 10.

The folded-back portion 80 in the example illustrated in FIG. 1 is formed over the entire main body 10 in the front-back direction LD by folding back the entire sheet on a backmost side of the main body 10 in the front-back direction LD. However, as in the folded-back portion 80 in the examples illustrated in FIGS. 15 to 18, by folding back only a part of the sheet on a backmost side of the main body 10 in the front-back direction LD, the folded-back portion 80 may be disposed only in a partial region including the site where the fastener folded-back portion 81 of the fastening tape 13 is located. Incidentally, in the latter embodiment, the folded-back portion 80 may be locally formed from the beginning. However, as in the examples illustrated in FIGS. 15 to 18, by forming the folded-back portion 80 extending in the front-back direction LD of the main body 10 at the time of assembly of the main body 10 and then cutting an intermediate portion of a side of the main body 10 in the front-back direction LD in order to form a wing portion in the main body 10, as a result, the folded-back portion 80 may be formed only in a part of the main body 10 in the front-back direction LD.

In a case where the connecting portion 13A of the fastener folded-back portion 81 is used for temporary fixing, as in the example illustrated in FIG. 11(a), the whole thereof may be temporarily fixed to the folded-back portion 80. However, as illustrated in the example illustrated in FIG. 11(b), the connecting portion 13A preferably has a temporarily fixed portion 13x temporarily fixed to the folded-back portion 80 and a projecting portion 13p located on a width direction WD center side of an edge of the folded-back portion 80 on a width direction WD center side and not temporarily fixed to the folded-back portion 80. In this way, when a part of the connecting portion 13A is located on a width direction WD center side of the folded-back portion 80 to form the projecting portion, the connecting portion 13A is easily peeled off when the fastener folded-back portion 81 is unfolded. In order to make temporary fixing of the fastener folded-back portion 81 sufficient, the maximum width of the temporarily fixed portion 13x is preferably 50% or more of the maximum width of the connecting portion 13A.

In a case where the connecting portion 13A is used for temporary fixing, the width of the folded-back portion 80 only needs to be wider than an interval between a side edge of the main body 10 and the connecting portion 13A of the fastening tape 13 in the width direction WD. For example, when the width of the folded-back portion 80 is equal to or larger than a length obtained by adding the size of the connecting portion 13A in the width direction WD to the interval between the side edge of the main body 10 and the connecting portion 13A of the fastening tape 13 in the width direction WD, the entire connecting portion 13A in the width direction WD can be temporarily fixed to the folded-back portion 80. When the width of the folded-back portion 80 is equal to a length obtained by adding a size shorter than the size of the connecting portion 13A in the width direction WD to the interval between the side edge of the main body 10 and the connecting portion 13A of the fastening tape 13 in the width direction WD, a part of the connecting portion 13A projects from the folded-back portion 80.

As illustrated in FIG. 14(a), preferably, the width of the gather sheet 62 is narrowed, and the gather sheet 62 is extended only to an end portion of the folded-back portion 80 on a center side in the width direction (an end portion of the gather sheet 62 on a base side is located at an end portion of the folded-back portion 80 on a center side in the width direction WD) because it is possible to reduce a region where the thickness is increased by overlapping between the folded-back portion 80 of the outer sheet 12 and the gather sheet 62 and to suppress a decrease in air permeability and flexibility. In an embodiment having the side gather, when one of the sheets sandwiching the side elastic member 70 is the gather sheet 62, it is difficult to narrow the width of the gather sheet 62. Therefore, as in the illustrated example, the side elastic member 70 is preferably disposed between the liquid impervious sheet 11 and a portion located on a back surface side of the main body 10 in the outer sheet 12.

As in the example illustrated in FIG. 14(b), an embodiment is also preferable in which the folded-back portion 80 extends to the rising portion 68 in the rising gather 60 and is bonded to the rising gather 60. When the outer side of the rising portion 68 of the rising gather 60 is covered with the folded-back portion 80, the number of stacked layers of a material of the rising gather 60 is increased, and a liquid impervious property of the rising gather 60 can be improved. In particular, as in the illustrated example, the present aspect is suitable in a the case where a water shielding film is not incorporated in rising gather 60.

Preferably, all the sheets or some of the sheets (the outer sheet 12 in the illustrated example) forming the folded-back portion 80 are formed of a perforated nonwoven fabric having many holes passing through the sheet from the front to the back at intervals, and have many holes at least in the folded-back portion 80 because it is possible to suppress a decrease in flexibility and air permeability. The size of each of the holes, the shape thereof, and the disposition thereof are not particularly limited. However, in a usual case, the area of each of the holes is preferably about 0.2 to 2.5 $mm^2$ (particularly 0.5 to 1.5 $mm^2$), and the area ratio is preferably about 1.0 to 15.0% (particularly 5.0 to 10.0%).

Explanation of Terms in Specification

The following terms in the specification have the following meanings unless otherwise specified in the specification.

"Unfolded state" means a state completely and completely flatly stretched and extended without contraction or slackness from a natural length state.

"Stretch rate" means a value obtained when a natural length is 100%.

"Gel strength" is measured as follows. To 49.0 g of artificial urine, 1.0 g of super absorbent polymer is added, and the resulting mixture is stirred with a stirrer. The gel thus generated is left in a thermohygrostat at 40° C.×60% RH for three hours. Thereafter, the temperature is returned to room temperature, and gel strength is measured with a curdmeter (Curdmeter-MAX ME-500 manufactured by I. Techno Engineering Co., Ltd.).

"Artificial urine" is 2 wt % urea, 0.8 wt % sodium chloride, 0.03 wt % calcium chloride dihydrate, 0.08 wt % magnesium sulfate heptahydrate, and 97.09 wt % ion-exchanged water It is a mixture and is used at a temperature of 37 degrees unless otherwise stated.

"Basis weight" is measured as follows. A sample or a test piece is predried and then left in a test chamber or an apparatus in a standard state (test location is at a temperature of 23±1° C. and a relative humidity of 50±2%) so as to have a constant weight. Predrying refers to causing a sample or a test piece to have a constant weight in an environment of a temperature of 100° C. Incidentally, fibers having an official moisture regain of 0.0% do not have to be predried. A sample of 100 mm×100 mm in size is cut out from a test piece having a constant weight using a template for sampling (100 mm×100 mm). The weight of the sample is measured. The weight is multiplied by 10 to calculate the weight per square meter to be used as a basis weight.

"Water absorption capacity" is measured in accordance with JIS K7223-1996 "Test method for water absorption capacity of super absorbent polymer".

"Water absorption rate" is "time to end point" when JIS K7224-1996 "Test method for water absorption rate of super absorbent polymer" is performed using 2 g of super absorbent polymer and 50 g of physiological saline.

In a case where environmental conditions in a test and a measurement are not described, the test and the measurement are performed in a test room or an apparatus in a standard state (test location is at a temperature of 23±1° C. and a relative humidity of 50±2%).

The size of each portion means a size not in a natural length state but in an unfolded state unless otherwise specified.

INDUSTRIAL APPLICABILITY

The present invention can be applied to such a tape-type disposable diaper as in the above example.

REFERENCE SIGNS LIST

10 Main body
11 Liquid impervious sheet
12 Outer sheet
12T Target sheet
13 Fastening tape
13A Connecting portion
13B Base portion
13E Tape stretchable region
13F Fastener free portion
30 Top sheet
40 Intermediate sheet
50 Absorbent element
56 Absorber
58 Wrapping sheet
60 Rising gather
62 Gather sheet
63 Gather elastic member
70 Side elastic member
B Dorsal side portion
F Ventral side portion
EF End flap portion
SF Side flap portion
LD Front-back direction
WD Width direction
80 Folded-back portion
81 Fastener folded-back portion
90 Waist stretching sheet
96 Non-stretchable region
95 Main body stretchable region

The invention claimed is:

1. A tape-type disposable diaper comprising:
a main body having a ventral side portion extending to a front side from a center in a front-back direction and a dorsal side portion extending to a back side from the center in the front-back direction;
fastening tapes protruding from both side portions of a lower torso portion of the dorsal side portion; and
a waist stretching sheet disposed in the lower torso portion of the dorsal side portion,
each of the fastening tapes having a base portion attached to the lower torso portion of the dorsal side portion and a connecting portion detachably connected to an outer surface of the ventral side portion,
the waist stretching sheet serving as a non-stretchable region at both end portions in the width direction and serving as a main body stretchable region that expands and contracts in the width direction at a portion between the non-stretchable regions,
wherein the main body has a folded-back portion obtained by folding back a side including a portion having the non-stretchable region to a center side and fixing thereto.

2. The tape-type disposable diaper according to claim 1, wherein each of the fastening tapes has a tape stretchable region that is disposed in a portion between the base portion and the connecting portion and expands and contracts in the width direction; and
the fastening tapes are attached to the main body such that a base edge of the tape stretchable region is located within a range of ±5 mm in the width direction from a side edge of the main body stretchable region.

3. The tape-type disposable diaper according to claim 2, wherein the main body includes:
an absorber;
a liquid impervious sheet covering a back surface side of the absorber;
an outer sheet covering a back surface side of the liquid impervious sheet;
side flap portions each located outside a side edge of the absorber; and
a rising gather including: a gather sheet forming a root portion fixed to a region including each of the side flap portions, and a protruding portion extending from the root portion; a fallen portion in which both end portions of the protruding portion in a front-back direction are fixed in a fallen state; a non-fixed rising portion located between front and back fallen portions in the protruding portion; and a gather elastic member fixed in a state of being stretched in the front-back direction at least at a tip portion of the rising portion,
the main body stretchable region in the waist stretching sheet extends across the left and right side flap portions,
each of the side flap portions is a portion in which the gather sheet, the liquid impervious sheet, the waist stretching sheet, and the outer sheet are stacked, the folded-back portion is formed in each of the side flap portions and is a portion in which the gather sheet, at least a part of the non-stretchable region of the waist stretching sheet, and the outer sheet are folded back to a front surface side, and a base portion of each of the fastening tapes is attached to a back surface of a portion having the folded-back portion in each of the side flap portions.

4. The tape-type disposable diaper according to claim 2, wherein the main body includes:
an absorber;
a liquid impervious sheet covering a back surface side of the absorber;
an outer sheet covering a back surface side of the liquid impervious sheet;
side flap portions each located outside a side edge of the absorber; and
a rising gather including: a gather sheet forming a root portion fixed to a region including each of the side flap portions, and a protruding portion extending from the root portion; a fallen portion in which both end portions of the protruding portion in a front-back direction are fixed in a fallen state; a non-fixed rising portion located between front and back fallen portions in the protruding portion; and a gather elastic member fixed in a state of being stretched in the front-back direction at least at a tip portion of the rising portion,
the main body stretchable region in the waist stretching sheet extends across the left and right side flap portions,
each of the side flap portions is a portion in which the gather sheet, the liquid impervious sheet, the waist stretching sheet, and the outer sheet are stacked,
the folded-back portion is formed in each of the side flap portions and is a portion in which at least a part of the non-stretchable region of the waist stretching sheet and the outer sheet are folded back to a front surface side,
a front surface side of the folded-back portion is covered with a side of the gather sheet, and
a base portion of the fastening tapes is attached between the folded-back portion and a side of the gather sheet in each of the side flap portions.

5. The tape-type disposable diaper according to claim 2, wherein the main body includes:
an absorber;
a liquid impervious sheet covering a back surface side of the absorber;
an outer sheet covering a back surface side of the liquid impervious sheet;
side flap portions each located outside a side edge of the absorber; and
a rising gather including: a gather sheet forming a root portion fixed to a region including each of the side flap portions, and a protruding portion extending from the root portion; a fallen portion in which both end portions of the protruding portion in a front-back direction are fixed in a fallen state; a non-fixed rising portion located between front and back fallen portions in the protruding portion; and a gather elastic member fixed in a state of being stretched in the front-back direction at least at a tip portion of the rising portion,
the main body stretchable region in the waist stretching sheet extends across the left and right side flap portions,
each of the side flap portions is a portion in which the gather sheet, the liquid impervious sheet, the waist stretching sheet, and the outer sheet are stacked,
the folded-back portion is formed in each of the side flap portions and is a portion in which the gather sheet, at least a part of the non-stretchable region of the waist stretching sheet, and the outer sheet are folded back to a back surface side, and
a base portion of each of the fastening tapes is attached to a back surface of a portion having the folded-back portion in each of the side flap portions.

6. The tape-type disposable diaper according to claim 3, wherein the folded-back portion does not include the liquid impervious sheet.

7. The tape-type disposable diaper according to claim 1, wherein each of the fastening tapes has the base portion fixed to a back surface of the main body and a fastener free portion extending in a lateral side from the base portion, the fastener free portion has a fastener folded-back portion folded back to an upper side of the folded-back portion at a side edge of the main body; and
the fastener folded-back portion is releasably and temporarily fixed to the folded-back portion of the main body at a portion overlapping with the folded-back portion of the main body.

8. The tape-type disposable diaper according to claim 7, wherein the fastener folded-back portion has the connecting portion at a portion overlapping with the folded-back portion of the main body,
the fastener folded-back portion is temporarily fixed to the folded-back portion of the main body by the connecting portion, and
the connecting portion has a temporarily fixed portion temporarily fixed to the folded-back portion of the main body and a projecting portion located on a width direction center side of a width direction center side edge of the folded-back portion of the main body and not temporarily fixed to the folded-back portion of the main body.

9. The tape-type disposable diaper according to claim 7, wherein the main body includes:
an absorber;
a liquid impervious sheet covering a back surface side of the absorber;
an outer sheet covering a back surface side of the liquid impervious sheet;
side flap portions each located outside a side edge of the absorber; and
a rising gather including: a gather sheet forming a root portion fixed to a region including each of the side flap portions, and a protruding portion extending from the root portion; a fallen portion in which both end portions of the protruding portion in a front-back direction are fixed in a fallen state; a non-fixed rising portion located between front and back fallen portions in the protruding portion; and a gather elastic member fixed in a state of being stretched in the front-back direction at least at a tip portion of the rising portion, and
the gather sheet extends only to an end portion on a width direction center side of the folded-back portion of the main body.

10. The tape-type disposable diaper according to claim 7, wherein the main body includes:
an absorber;
a liquid impervious sheet covering a back surface side of the absorber;
an outer sheet covering a back surface side of the liquid impervious sheet;
side flap portions each located outside a side edge of the absorber; and
a rising gather including: a gather sheet forming a root portion fixed to a region including each of the side flap portions, and a protruding portion extending from the root portion; a fallen portion in which both end portions of the protruding portion in a front-back direction are fixed in a fallen state; a non-fixed rising portion located between front and back fallen portions in the protruding portion; and a gather elastic member fixed in a state of being stretched in the front-back direction at least at a tip portion of the rising portion, and the folded-back portion of the main body extends to the rising portion of the rising gather and is bonded to the rising gather.

11. The tape-type disposable diaper according to claim 7, wherein a sheet on a backmost side of the main body is formed of a perforated nonwoven fabric having many holes passing through the sheet from the front to the back at intervals, and at least the folded-back portion of the main body has the many holes.

12. The tape-type disposable diaper according to claim 7, wherein the folded-back portion of the main body is bonded to a sheet adjacent to a back surface side of the folded-back portion of the main body via a hot melt adhesive disposed in an intermittent pattern.

13. A method for manufacturing the tape-type disposable diaper according to claim 7, the method comprising:

disposing the fastening tapes on the main body such that a site serving as a base portion of each of the fastening tapes is located at a site serving as a back surface side of the main body and extends to a site serving as the folded-back portion of the main body in an unfolded state before the folded-back portion of the main body is formed, fixing the site serving as the base portion of each of the fastening tapes to the main body, and releasably and temporarily fixing the fastening tape to the site serving as the folded-back portion of the main body; and folding back both side portions of the main body and the fastening tapes integrally to form the folded-back portion of the main body and the fastener folded-back portion.

14. The tape-type disposable diaper according to claim 4, wherein the folded-back portion does not include the liquid impervious sheet.

15. The tape-type disposable diaper according to claim 5, wherein the folded-back portion does not include the liquid impervious sheet.

* * * * *